US008871206B2

(12) United States Patent
Low et al.

(10) Patent No.: US 8,871,206 B2
(45) Date of Patent: Oct. 28, 2014

(54) ANTI-HUMAN FOLATE RECEPTOR BETA ANTIBODIES AND METHODS OF USE

(71) Applicants: Purdue Research Foundation, West Lafayette, IN (US); The United States of America, as Represented by the Secretary Department of Health and Human Services, Washington, DC (US)

(72) Inventors: Philip S. Low, West Lafayette, IN (US); Dimiter S. Dimitrov, Frederick, MD (US); Yang Feng, Frederick, MD (US); Jiayin Shen, San Diego, CA (US)

(73) Assignees: Purdue Research Foundation, West Lafayette, IN (US); The United States of America, as Represented by the Secretary Department of Health and Human Services, Washington, DC (US)

( * ) Notice: Subject to any disclaimer, the term of this patent is extended or adjusted under 35 U.S.C. 154(b) by 0 days.

(21) Appl. No.: 13/790,881

(22) Filed: Mar. 8, 2013

(65) Prior Publication Data
US 2013/0177570 A1 Jul. 11, 2013

Related U.S. Application Data

(63) Continuation of application No. PCT/US2011/050943, filed on Sep. 9, 2011.

(60) Provisional application No. 61/381,340, filed on Sep. 9, 2010.

(51) Int. Cl.
| | |
|---|---|
| C07K 16/28 | (2006.01) |
| A61K 47/48 | (2006.01) |
| A61K 49/16 | (2006.01) |
| A61K 9/127 | (2006.01) |
| A61K 49/00 | (2006.01) |
| A61K 38/00 | (2006.01) |
| A61K 51/10 | (2006.01) |
| C07K 14/705 | (2006.01) |
| A61K 9/00 | (2006.01) |

(52) U.S. Cl.
CPC ........... *C07K 16/28* (2013.01); *A61K 47/48561* (2013.01); *A61K 47/48823* (2013.01); *A61K 49/16* (2013.01); *C07K 2317/33* (2013.01); *A61K 9/127* (2013.01); *C07K 2317/54* (2013.01); *A61K 49/0058* (2013.01); *A61K 38/00* (2013.01); *A61K 51/1027* (2013.01); *C07K 2317/21* (2013.01); *C07K 14/705* (2013.01); *A61K 9/0019* (2013.01); *C07K 2317/92* (2013.01)
USPC .................. 424/139.1; 530/387.3; 530/387.9

(58) Field of Classification Search
None
See application file for complete search history.

(56) References Cited

U.S. PATENT DOCUMENTS

2008/0260812 A1* 10/2008 Matsuyama et al. .......... 424/450

OTHER PUBLICATIONS

Antohe et al, "Increased uptake of folate conjugates by activated macrophages in experimental hyperlipemia," *Cell Tissue Res.*, 320:277-285, Feb. 16, 2005.
Antony, "The biological chemistry of folate receptors," *Blood*, 79(11):2807-2820, Jun. 1, 1992.
Ayala-Lopez et al., "Imaging of atherosclerosis in apoliprotein e knockout mice: targeting of a folate-conjugated radiopharmaceutical to activated macrophages," *J Nuc Med*, 51(5):768-774 Epub Apr. 15, 2010.
Bender et al., "Recombinant human antibodies: linkage of an Fab fragment from a combinatorial library to an Fc fragment for expression in mammalian cell culture," *Hum Antibodies Hybridomas*, 4(2):74-79, Apr. 1993.
Blaser et al., "Induction of folate receptor type beta in a bone marrow engraftment model of acute myelogenous leukemia," *Leukemia*, 21:2233-2235, Epub Jun. 7, 2007.
Boerner et al., "Production of antigen-specific human monoclonal antibodies from in vitro-primed human splenocytes," *J. Immunol.*, 147(1): 86-95, Jul. 1, 1991.
Brown et al., "P38 MAP kinase inhibitors as potential therapeutics for the treatment of joint degeneration and pain associated with osteoarthritis," *J. Inflamm.* (Lond.), 5:22, Dec. 4, 2008.
Chaudhary et al., "A proper amino terminus of diphtheria toxin is important for cytotoxicity," *Biochem Biophys Res Commun.*, 180(2):545-551, Oct. 31, 1991.
Chen et al, "Detection of dysplastic intestinal adenomas using a fluorescent folate imaging probe," *Mol Imaging.* 4(1):67-74, Jan.-Mar. 2005.
Chen et al., "Arthritis imaging using a near-infrared fluorescence folate-targeted probe," *Arthritis Res Ther.*, 7(2):R310-317, Epub Jan. 14, 2005.
Elnakat and Ratnam, "Distribution, functionality and gene regulation of folate receptor isoforms: implications in targeted therapy," *Adv Drug Deliv Rev* 56(8):1067-1084, Apr. 29, 2004.
Eshhar, "The T-Body Approach: Redirecting T Cells with Antibody Specificity," *Therapeutic Antibodies (Handbook of Experimental Pharmacology)*: 181 Chernajovsky and Nissim (eds.), pp. 329-342, Dec. 13, 2007.
Feng et al., "A folate receptor beta-specific human monoclonal antibody recognizes activated macrophage of rheumatoid patients and mediates antibodydependent cell-mediated cytotoxicity," *Arthritis Research & Therapy*, 13:R59, 2011.

(Continued)

*Primary Examiner* — Brian J. Gangle
*Assistant Examiner* — Andrea McCollum
(74) *Attorney, Agent, or Firm* — Fish & Richardson P.C.

(57) ABSTRACT

Human anti-human folate receptor beta (FRβ) antibodies and antigen-binding fragments thereof are described, as well as methods of using such antibodies and fragments to treat inflammatory disorders or cancers expressing cell surface FRβ.

17 Claims, 12 Drawing Sheets

(56) References Cited

OTHER PUBLICATIONS

GenBank Accession No. 1VGE_H GI:1633497, "Chain H, Trl.9 Fab Fragment of a Human Igg1 Kappa Autoantibody," Jan. 4, 1996, 2 pages.
GenBank Accession No. AAF20601 GI:6643485, "Immunoglobulin lambda light chain variable region" [*Homo sapiens*], Jan. 10, 2000, 2 pages.
GenBank Accession No. ABF83408 GI:106899064, "Circulating B cell antibody heavy chain variable region, partial" [*Homo sapiens*], Feb. 1, 2007, 2 pages.
GenBank Accession No. BAC01838 GI:21669627 "Immunoglobulin lambda light chain VLJ region" [*Homo sapiens*], Jul. 2, 2002, 2 pages.
GenBank Accession No. NP_001107007 GI: 166064054, "Folate receptor 2 precursor [*Homo sapiens*]" 2 pages, Sep. 3, 2009.
Hassan et al., "Anti-tumor activity of K1-LysPE38QQR, an immunotoxin targeting mesothelin, a cell-surface antigen overexpressed in ovarian cancer and malignant mesothelioma," *J Immunother.*, 23(4):473-479, Jul.-Aug. 2000.
Hayashi et al., "Genetic polymorphisms in folate pathway enzymes as a possible marker for predicting the outcome of methotrexate therapy in Japanese patients with rheumatoid arthritis," *J Clin Pharm Ther.*, 34(3):355-361, Jun. 2009.
Hoogenboom and Chames, "Natural and designer binding sites made by phage display technology," *Immunol Today* 21(8):371-378, Aug. 2000.
Hoogenboom et al., "Antibody phage display technology and its applications," *Immunotechnology*, 4(1):1-20, Jun. 1998.
Houde et al., "Post-translational modifications differentially affect IgG1 conformation and receptor binding," *Mol Cell Proteomics.*, 9(8):1716-1728, Epub Jan. 26, 2010.
Huang and Stollar, "Construction of representative immunoglobulin variable region cDNA libraries from human peripheral blood lymphocytes without in vitro stimulation," *J. Immunol. Methods*, 141(2):227-236, Aug. 9, 1991.
Hudson and Kortt, "High avidity scFv multimers; diabodies and triabodies," *J Immunol Methods*, 231(1-2):177-189, Dec. 10, 1999.
Huston and George, "Engineered antibodies take center stage," *Hum. Antibodies*, 10(3-4):127-142, 2001.
Ischida et al., "Production of human monoclonal and polyclonal antibodies in TransChromo animals," *Cloning Stem Cells*, 4(1):91-102, 2002.
Ishiguro et al., "A defucosylated anti-CD317 antibody exhibited enhanced antibody-dependent cellular cytotoxicity against primary myeloma cells in the presence of effectors from patients," *Cancer Sci.*, 101(10):2227-2233, Epub Aug. 5, 2010.
Junttila et al., "Superior in vivo efficacy of afucosylated trastuzumab in the treatment of HER2-amplified breast cancer," *Cancer Res.*, 70(11):4481-9. Epub May 18, 2010.
Kim, "Nutritional epigenetics: impact of folate deficiency on DNA methylation and colon cancer susceptibility," *J Nutr.*, 135(11):2703-2709, Nov. 2005.
Kreitman, "Recombinant immunotoxins containing truncated bacterial toxins for the treatment of hematologic malignancies," *BioDrugs*, 23(1):1-13, 2009.
Kubota et al., "Engineered therapeutic antibodies with improved effector functions," *Cancer Sci.*, 100(9): 1566-1572, Epub May 18, 2009.
Leamon and Jackman, "Exploitation of the folate receptor in the management of cancer and inflammatory disease," *Vitam Horm.*, 79:203-233, 2008.
Loenen, "S-adenosylmethionine: jack of all trades and master of everything?" *Biochem Soc Trans*, 34(Pt 2):330-333, Apr. 2006.
Lonberg, "Fully human antibodies from transgenic mouse and phage display platforms," *Curr Opin Immunol.*, 20(4):450-459. Epub Jul. 21, 2008.
Low et al., "Discovery and development of folic-acid-based receptor targeting for imaging and therapy of cancer and inflammatory diseases," *Acc Chem Res*, 41(1):120-129, Epub Jul. 27, 2007.

Maira et al., "PI3K inhibitors for cancer treatment: where do we stand?, " *Biochem. Soc. Trans.*, 37(Pt 1): 265-272, Feb. 2009.
Malphettes et al., "Highly efficient deletion of FUT8 in CHO cell lines using zinc-finger nucleases yields cells that produce completely nonfucosylated antibodies," *Biotechnol. Bioeng.*, 106(5):774-783, Aug. 1, 2010.
Matherly and Goldman, "Membrane transport of folates," *Vitam Horm.*, 66:403-456, 2003.
Matteson et al., "Assessment of disease activity in rheumatoid arthritis using a novel folate targeted radiopharmaceutical Folatescan," *Clin Exp Rheumatol* 27(2):253-259, Mar.-Apr. 2009.
Nagai et al., "Effect of an immunotoxin to folate receptor beta on bleomjycin-induced experimental pulmonary fibrosis," *Clin Exp Immunol.*, 161(2):348-356, Epub Jun. 9, 2010.
Nagai et al., "In vitro and in vivo efficacy of a recombinant immunotoxin against folate receptor beta on the activation and proliferation of rheumatoid arthritis synovial cells," *Arthritis Rheum.*, 54(10):3126-3134, Oct. 2006.
Nagai et al., "Targeting tumor-associated macrophages in an experimental glioma model with a recombinant immunotoxin to folate receptor beta," *Cancer Immunol Immunother.*, 58(10):1577-1586, Oct. 2009.
Nagayoshi et al., "Effectiveness of anti-folate receptor beta antibody conjugated with truncated *Pseudomonas* exotoxin in the targeting of rheumatoid arthritis synovial macrophages," *Arthritis Rheum.*, 52(9):2666-2675, Sep. 2005.
Nakamura et al., "Nitration and chlorination of folic acid by peroxynitrite and hypochlorous acid, and the selective binding of 10-nitro-folate to folate receptor beta," *Biochem Biophys Res Commun.*, 297(5):1238-1244, Oct. 11, 2002.
Nakashima-Matsushita et al., "Selective expression of folate receptor beta and its possible role in methotrexate transport in synovial macrophages from patients with rheumatoid arthritis," *Arth Rheum.*, 42(8):1609-1616, Aug. 1999.
Natsume et al., "Improving effector functions of antibodies for cancer treatment: Enhancing ADCC and CDC," *Drug Des. Develop. Ther.*, 3:7-16, Sep. 21, 2009.
Parker et al., "Folate receptor expression in carcinomas and normal tissues determined by a quantitative radioligand binding assay," *Anal Biochem* 338(2):284-293, Mar. 15, 2005.
Paulos et al., "Folate receptor-mediated targeting of therapeutic and imaging agents to activated macrophages in rheumatoid arthritis," *Adv Drug Deliv Rev* 56(8):1205-1217, Apr. 29, 2004.
Paulos et al., "Folate-targeted immunotherapy effectively treats established adjuvant and collagen-induced arthritis," *Arthritis Res Ther.*, 8(3):R77, Epub Apr. 28, 2006.
Peinert et al., "Chimeric T cells for adoptive immunotherapy of cancer: using what have we learned to plan for the future," *Immunotherapy*, 1(6): 905-912, Nov. 2009.
Persson et al., "Generation of diverse high-affinity human monoclonal antibodies by repertoire cloning," *Proc. Nat. Acad. Sci. USA*, 88(6): 2432-2436, Mar. 15, 1991.
Poljak, "Production and structure of diabodies," *Structure*, 2(12):1121-1123, Dec. 15, 1994.
Porcheray et al., "Macrophage activation switching: an asset for the resolution of inflammation," *Clin Exp Immunol.* 143(3): 481-489, Dec. 2005.
Puig-Kröger et al., "Folate receptor beta is expressed by tumor-associated macrophages and constitutes a marker for M2 anti-inflammatory/regulatory macrophages," *Cancer Res.*, 69(24):9395-9403, Dec. 15, 2009.
Raju, "Terminal sugars of Fc glycans influence antibody effector functions of IgGs," *Curr. Opin. Immunol.*, 20(4):471-478, Aug. 2008.
Reddy et al., "Expression and functional characterization of the beta-isoform of the folate receptor on CD34(+) cells," *Blood*, 93(11):3940-3948, Jun. 1, 1999.
Ross et al, (1999) "Folate receptor type β is a neutrophilic lineage marker and is differentially expressed in myeloid leukemia," *Cancer* 85(2):348-357, Jan. 15, 1999.
Ross et al., "Differential regulation of folate receptor isoforms in normal and malignant tissues in vivo and in established cell lines. Physiologic and clinical implications," *Cancer*, 73:2432-2443, May 1, 1994.

(56) References Cited

OTHER PUBLICATIONS

Saborowski et al., "MR imaging of antigen-induced arthritis with a new, folate receptor-targeted contrast agent," *Contrast Media Mol Imaging* 2(2):72-81, Mar.-Apr. 2007.

Salazar and Ratnam, "The folate receptor: what does it promise in tissue-targeted therapeutics?" *Cancer Mestastasis Rev* 26(1):141-152, Mar. 2007.

Sandoval et al., "Uptake and trafficking of fluorescent conjugates of folic acid in intact kidney determined using intravital two-photon microscopy," *Am J Cell Physiol.*, 287(2):C517-C526, Epub Apr. 21, 2004.

Stocks, "Intrabodies: production and promise," *Drug Discov. Today*, 9(22): 960-966, Nov. 15, 2004.

Turk et al., "Folate-conjugated liposomes preferentially target macrophages associated with ovarian carcinoma," *Cancer Lett.*, 213(2):165-172, Sep. 30, 2004.

Turk et al., "Folate-targeted imaging of activated macrophages in rats with adjuvant-induced arthritis," *Arthritis Rheum.*, 46(7):1947-1955, Jul. 2002.

van der Heijden et al., "Folate receptor beta as a potential delivery route for novel folate antagonists to macrophages in the synovial tissue of rheumatoid arthritis patients," *Arth Rheum*, 60(1):12-21, Jan. 2009.

Varghese et al., "Depletion of folate-receptor-positive macrophages leads to alleviation of symptoms and prolonged survival in two murine models of systemic lupus erythematosus," *Mol Pharm.*, 4(5):679-685, Epub Sep. 12, 2007.

von Horsten et al., "Production of non-fucosylated antibodies by co-expression of heterologous GDP-6-deoxy-D-lyxo-4-hexulose reductase," *Glycobiology*, 20(12):1607-1618, Epub Jul. 15, 2010.

Weitman et al., "Cellular localization of the folate receptor: potential role in drug toxicity and folate homeostasis," *Cancer Res.*, 52(53):6708-6711, Dec. 1, 1992.

Wheeler et al., "Intrabody and intrakine strategies for molecular therapy," *Mol. Ther.* 8(3):355-366, Sep. 2003.

Wong et al., "Enhancement of DNA uptake in FUT8-deleted CHO cells for transient production of afucosylated antibodies," *Biotechnol Bioeng.*, 106(5):751-763, Aug. 1, 2010.

Xia et al., "A functional folate receptor is induced during macrophage activiation and can be used to target drugs to activated macrophages," *Blood*, 113:438-446, Jan. 2009.

Yamane-Ohnuki and Satoh, "Production of therapeutic antibodies with controlled fucosylation," *mAbs*, 1:3: 230-236; May/Jun. 2009.

Yi et al., "Folate-targeted hapten immunotherapy of adjuvant-induced arthritis: comparison of hapten potencies," *Mol Pharm.*, 6(4):1228-1236, Jul.-Aug. 2009.

Zeyda et al., "Human adipose tissue macrophages are of an anti-inflammatory phenotype but capable of excessive pro-inflammatory mediator production," *Int J Obes* (Lond)., 31(9):1420-1428, Epub Jun. 26, 2007.

International Search Report and Written Opinion for PCT/US2011/050943, mailed Aug. 28, 2012, 16 pages.

International Preliminary Report on Patentability for PCT/US2011/050943, issued Mar. 12, 2013, 8 pages.

European Search Report for EP App. No. 11824164.5 dated Jan. 21, 2014, 7 pages.

\* cited by examiner

```
  1  MVWKWMPLLLLLVCVATMCSAQDRTDLLNVCMDAKHHKTKPGPEDKLHDQCSPWKKNACC
 61  TASTSQELHKDTSRLYNFNWDHCGKMEPACKRHFIQDTCLYECSPNLGPWIQQVNQSWRK
121  ERFLDVPLCKEDCQRWWEDCHTSHTCKSNWHRGWDWTSGVNKCPAGALCRTFESYFPTPA
181  ALCEGLWSHSYKVSNYSRGSGRCIQMWFDSAQGNPNEEVARFYAAAMHVNAGEMLHGTGG
241  LLLSLALMLQ LWLLG (SEQ ID NO:9)
```

M909 heavy chain sequence

*EVQLVQSGAEVKKPGASVKVSCKAS*<u>GYTFTSYAMH</u>*WVRQAPG QRLEWMGW*<u>INAGNGNTKYSQKFQG</u>*RVTITRDTSASTAYMELS SLRSEDTAVYYC*<u>ARDISYGSFDY</u>*WGQGTLVTVSS*astkgpsvfplap sskstsggtaalgclvkdyfpepvtvswnsgaltsgvhtfpavlqssglyslssvvtvpsssl gtqtyicnvnhkpsntkvdkkvepkscdktsgqag

FIGURE 2B

M909 light chain sequence

*SSELTQDPAVSVALGQTVRITCQGD*<u>SLRSNY</u>*ANWYQQKPGQA PVLVIY*<u>GQN</u><u>N</u>*RPSGIPDRFSGSSSGNTASLTITGAQAADEADYYC* <u>DSRVSTGNHVVF</u>*GGGTKLTVL*gqpkaapsvtlfppsseelqankatlvclis dfypgavtvakadsspvkagvetttpskqsnnkyaassylsltpeqwkshrsyscqvtheg stvektvaptecs

SEQUENCE LISTING

<160> NUMBER OF SEQ ID NOS: 21

<210> SEQ ID NO 1
<211> LENGTH: 8
<212> TYPE: PRT
<213> ORGANISM: Artificial Sequence
<220> FEATURE:
<223> OTHER INFORMATION: heavy chain complementarity determining region from a human anti-human FR beta antibody

<400> SEQUENCE: 1

Gly Tyr Thr Phe Thr Ser Tyr Ala
 1               5

<210> SEQ ID NO 2
<211> LENGTH: 7
<212> TYPE: PRT
<213> ORGANISM: Artificial Sequence
<220> FEATURE:
<223> OTHER INFORMATION: heavy chain complementarity determining region from a human anti-human FR beta antibody

<400> SEQUENCE: 2

Lys Tyr Ser Gln Lys Phe Gln
 1               5

<210> SEQ ID NO 3
<211> LENGTH: 12
<212> TYPE: PRT
<213> ORGANISM: Artificial Sequence
<220> FEATURE:
<223> OTHER INFORMATION: heavy chain complementarity determining region from a human anti-human FR beta antibody

<400> SEQUENCE: 3

Ala Arg Asp Ile Ser Tyr Gly Ser Phe Asp Tyr Trp
 1               5                   10

<210> SEQ ID NO 4
<211> LENGTH: 6
<212> TYPE: PRT
<213> ORGANISM: Artificial Sequence
<220> FEATURE:
<223> OTHER INFORMATION: light chain complementarity determining region from a human anti-human FR beta antibody

<400> SEQUENCE: 4

Asn Leu Arg Ser Tyr Tyr
 1               5

<210> SEQ ID NO 5
<211> LENGTH: 3
<212> TYPE: PRT
<213> ORGANISM: Artificial Sequence
<220> FEATURE:
<223> OTHER INFORMATION: light chain complementarity determining region from a human anti-human FR beta antibody

<400> SEQUENCE: 5

Gly Lys Asn
 1

<210> SEQ ID NO 6
<211> LENGTH: 12
<212> TYPE: PRT
<213> ORGANISM: Artificial Sequence
<220> FEATURE:
<223> OTHER INFORMATION: light chain complementarity determining region from a human anti-human FR beta antibody

<400> SEQUENCE: 6

His Ser Arg Lys Ser Arg Gly Asn His Leu Leu Phe
1               5                   10

<210> SEQ ID NO 7
<211> LENGTH: 229
<212> TYPE: PRT
<213> ORGANISM: Artificial Sequence
<220> FEATURE:
<223> OTHER INFORMATION: heavy chain sequence from a human anti-human FR
      beta antibody

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ile Ser Tyr Gly Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

Ser Gly Gln Ala Gly
225

<210> SEQ ID NO 8
<211> LENGTH: 213
<212> TYPE: PRT
<213> ORGANISM: Artificial Sequence
<220> FEATURE:
<223> OTHER INFORMATION: lambda light chain sequence from a human
      anti-human FR beta antibody

<400> SEQUENCE: 8

Ser Ser Glu Leu Thr Gln Asp Pro Ala Val Ser Val Ala Leu Gly Gln
1               5                   10                  15

Thr Val Arg Ile Thr Cys Gln Gly Asp Asn Leu Arg Ser Tyr Tyr Ala
                20                  25                  30

```
Ser Trp Tyr Arg Gln Lys Ser Gly Gln Ala Pro Val Leu Val Ile Tyr
         35                  40                  45

Gly Lys Asn Asn Arg Pro Ser Gly Ile Pro Asp Arg Phe Ser Gly Ser
     50                  55                  60

Ser Ser Gly Asn Thr Ala Ser Leu Thr Ile Thr Ala Ala Gln Ala Glu
 65                  70                  75                  80

Asp Glu Ala Asp Tyr Tyr Cys His Ser Arg Lys Ser Arg Gly Asn His
                 85                  90                  95

Leu Leu Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                 165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
        210

<210> SEQ ID NO 9
<211> LENGTH: 255
<212> TYPE: PRT
<213> ORGANISM: Homo sapiens

<400> SEQUENCE: 9

Met Val Trp Lys Trp Met Pro Leu Leu Leu Leu Val Cys Val Ala
  1               5                  10                  15

Thr Met Cys Ser Ala Gln Asp Arg Thr Asp Leu Leu Asn Val Cys Met
             20                  25                  30

Asp Ala Lys His His Lys Thr Lys Pro Gly Pro Glu Asp Lys Leu His
         35                  40                  45

Asp Gln Cys Ser Pro Trp Lys Lys Asn Ala Cys Cys Thr Ala Ser Thr
     50                  55                  60

Ser Gln Glu Leu His Lys Asp Thr Ser Arg Leu Tyr Asn Phe Asn Trp
 65                  70                  75                  80

Asp His Cys Gly Lys Met Glu Pro Ala Cys Lys Arg His Phe Ile Gln
                 85                  90                  95

Asp Thr Cys Leu Tyr Glu Cys Ser Pro Asn Leu Gly Pro Trp Ile Gln
            100                 105                 110

Gln Val Asn Gln Ser Trp Arg Lys Glu Arg Phe Leu Asp Val Pro Leu
            115                 120                 125

Cys Lys Glu Asp Cys Gln Arg Trp Trp Glu Asp Cys His Thr Ser His
        130                 135                 140

Thr Cys Lys Ser Asn Trp His Arg Gly Trp Asp Trp Thr Ser Gly Val
145                 150                 155                 160

Asn Lys Cys Pro Ala Gly Ala Leu Cys Arg Thr Phe Glu Ser Tyr Phe
                 165                 170                 175

Pro Thr Pro Ala Ala Leu Cys Glu Gly Leu Trp Ser His Ser Tyr Lys
```

```
                180             185             190
Val Ser Asn Tyr Ser Arg Gly Ser Gly Arg Cys Ile Gln Met Trp Phe
            195             200             205

Asp Ser Ala Gln Gly Asn Pro Asn Glu Glu Val Ala Arg Phe Tyr Ala
    210             215             220

Ala Ala Met His Val Asn Ala Gly Glu Met Leu His Gly Thr Gly Gly
225             230             235             240

Leu Leu Leu Ser Leu Ala Leu Met Leu Gln Trp Leu Leu Gly
            245             250             255

<210> SEQ ID NO 10
<211> LENGTH: 118
<212> TYPE: PRT
<213> ORGANISM: Artificial Sequence
<220> FEATURE:
<223> OTHER INFORMATION: heavy chain sequence from a human anti-human FR
      beta antibody

<400> SEQUENCE: 10

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ile Ser Tyr Gly Ser Phe Asp Tyr Trp Gly Gln Gly Thr
            100                 105                 110

Leu Val Thr Val Ser Ser
        115

<210> SEQ ID NO 11
<211> LENGTH: 108
<212> TYPE: PRT
<213> ORGANISM: Artificial Sequence
<220> FEATURE:
<223> OTHER INFORMATION: lambda light chain sequence from a human
      anti-human FR beta antibody

<400> SEQUENCE: 11

Ser Ser Glu Leu Thr Gln Asp Pro Ala Val Ser Val Ala Leu Gly Gln
1               5                   10                  15

Thr Val Arg Ile Thr Cys Gln Gly Asp Asn Leu Arg Ser Tyr Tyr Ala
            20                  25                  30

Ser Trp Tyr Arg Gln Lys Ser Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Ala Ala Gln Ala Glu
65                  70                  75                  80

Asp Glu Ala Asp Tyr Tyr Cys His Ser Arg Lys Ser Arg Gly Asn His
                85                  90                  95

Leu Leu Phe Gly Gly Gly Thr Lys Leu Thr Val Leu
```

100                 105

<210> SEQ ID NO 12
<211> LENGTH: 4
<212> TYPE: PRT
<213> ORGANISM: Artificial Sequence
<220> FEATURE:
<223> OTHER INFORMATION: N-terminal amino acids from recombinantly
      produced FR beta

<400> SEQUENCE: 12

Ala Asp Pro Gly
 1

<210> SEQ ID NO 13
<211> LENGTH: 5
<212> TYPE: PRT
<213> ORGANISM: Artificial Sequence
<220> FEATURE:
<223> OTHER INFORMATION: linker on single chain form of m909

<400> SEQUENCE: 13

Gly Gly Gly Gly Ser
 1               5

<210> SEQ ID NO 14
<211> LENGTH: 6
<212> TYPE: PRT
<213> ORGANISM: Artificial Sequence
<220> FEATURE:
<223> OTHER INFORMATION: light chain complementarity determining region
      from a human anti-human FR beta antibody

<400> SEQUENCE: 14

Ser Leu Arg Ser Asn Tyr
 1               5

<210> SEQ ID NO 15
<211> LENGTH: 3
<212> TYPE: PRT
<213> ORGANISM: Artificial Sequence
<220> FEATURE:
<223> OTHER INFORMATION: light chain complementarity determining region
      from a human anti-human FR beta antibody

<400> SEQUENCE: 15

Gly Gln Asn
 1

<210> SEQ ID NO 16
<211> LENGTH: 12
<212> TYPE: PRT
<213> ORGANISM: Artificial Sequence
<220> FEATURE:
<223> OTHER INFORMATION: light chain complementarity determining region
      from a human anti-human FR beta antibody

<400> SEQUENCE: 16

Asp Ser Arg Val Ser Thr Gly Asn His Val Val Phe
 1               5                  10

<210> SEQ ID NO 17
<211> LENGTH: 213
<212> TYPE: PRT
<213> ORGANISM: Artificial Sequence
<220> FEATURE:
<223> OTHER INFORMATION: lambda light chain sequence from a human
      anti-human FR beta antibody

<400> SEQUENCE: 17

```
Ser Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg Ser Asn Tyr Ala
             20                  25                  30

Asn Trp Tyr Gln Gln Lys Pro Gly Gln Ala Pro Val Leu Val Ile Tyr
         35                  40                  45

Gly Gln Asn Asn Arg Pro Ser Gly Ile Pro Asp Arg Phe Ser Gly Ser
     50                  55                  60

Ser Ser Gly Asn Thr Ala Ser Leu Thr Ile Thr Gly Ala Gln Ala Ala
 65                  70                  75                  80

Asp Glu Ala Asp Tyr Tyr Cys Asp Ser Arg Val Ser Thr Gly Asn His
                 85                  90                  95

Val Val Phe Gly Gly Gly Thr Lys Leu Thr Val Leu Gly Gln Pro Lys
             100                 105                 110

Ala Ala Pro Ser Val Thr Leu Phe Pro Pro Ser Ser Glu Glu Leu Gln
         115                 120                 125

Ala Asn Lys Ala Thr Leu Val Cys Leu Ile Ser Asp Phe Tyr Pro Gly
    130                 135                 140

Ala Val Thr Val Ala Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

<210> SEQ ID NO 18
<211> LENGTH: 108
<212> TYPE: PRT
<213> ORGANISM: Artificial Sequence
<220> FEATURE:
<223> OTHER INFORMATION: lambda light chain sequence from a human anti-human FR beta antibody

<400> SEQUENCE: 18

```
Ser Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg Ser Asn Tyr Ala
             20                  25                  30

Asn Trp Tyr Gln Gln Lys Pro Gly Gln Ala Pro Val Leu Val Ile Tyr
         35                  40                  45

Gly Gln Asn Asn Arg Pro Ser Gly Ile Pro Asp Arg Phe Ser Gly Ser
     50                  55                  60

Ser Ser Gly Asn Thr Ala Ser Leu Thr Ile Thr Gly Ala Gln Ala Ala
 65                  70                  75                  80

Asp Glu Ala Asp Tyr Tyr Cys Asp Ser Arg Val Ser Thr Gly Asn His
                 85                  90                  95

Val Val Phe Gly Gly Gly Thr Lys Leu Thr Val Leu
             100                 105
```

<210> SEQ ID NO 19

<211> LENGTH: 688
<212> TYPE: DNA
<213> ORGANISM: Artificial Sequence
<220> FEATURE:
<223> OTHER INFORMATION: nucleotide sequence encoding m909 heavy chain

<400> SEQUENCE: 19

```
cgaagtgcag ctggtgcagt ctggggctga ggtgaagaag cctggggcct cagtgaaggt      60
ttcctgcaag gcttctggat acaccttcac tagctatgct atgcattggg tgcgccaggc     120
ccccggacaa aggcttgagt ggatgggatg gatcaacgct ggcaatggta acacaaaata    180
ttcacagaag ttccagggca gagtcaccat taccagggac acatccgcga gcacagccta    240
catggagctg agcagcctga gatctgaaga cacggctgtg tattactgtg cgagagacat    300
cagctatggt tcgtttgact actggggcca gggaaccctg gtcaccgtct cctcagcctc    360
caccaagggc ccatcggtct tccccctggc accctcctcc aagagcacct ctgggggcac    420
agcggccctg gctgcctggt caaggactac ttccccgaa ccggtgacgg tgtcgtggaa    480
ctcaggcgcc ctgaccagcg gcgtgcacac cttcccggct gtcctacagt cctcaggact    540
ctactccctc agcagcgtgg tgaccgtgcc ctccagcagc ttgggcaccc agacctacat    600
ctgcaacgtg aatcacaagc ccagcaacac caaggtggac aagaaagttg agcccaaatc    660
ttgtgacaaa actagtggcc aggccggc                                        688
```

<210> SEQ ID NO 20
<211> LENGTH: 653
<212> TYPE: DNA
<213> ORGANISM: Artificial Sequence
<220> FEATURE:
<223> OTHER INFORMATION: nucleotide sequence encoding m923 light chain

<400> SEQUENCE: 20

```
gcctcttctg agctgactca ggaccctgct gtgtctgtgg ccttgggaca gacagtcagg      60
atcacatgcc aaggagacaa cctcagaagc tattatgcaa gctggtaccg gcagaagtca    120
ggacaggccc ctgtacttgt catctatggt aaaaacaacc ggccctcagg gatcccagac    180
cgattctctg gctccagctc aggaaacaca gcttccttga ccatcactgc ggctcaggcg    240
gaagatgagg ctgactatta ctgtcactcc cggaaaagcc gcggtaacca tctgctattc    300
ggcggaggga ccaagctgac cgtcctaggt cagcccaagg ctgccccctc ggtcactctg    360
ttcccgccct cctctgagga gcttcaagcc aacaaggcca cactggtgtg tctcataagt    420
gacttctacc cgggagccgt gacagtggcc tggaaggcag atagcagccc cgtcaaggcg    480
ggagtggaga ccaccacacc ctccaaacaa gcaacaaca agtacgcggc cagcagctat    540
ctgagcctga cgcctgagca gtggaagtcc cacagaagct acagctgcca ggtcacgcat    600
gaagggagca ccgtggagaa gacagtggcc cctacagaat gttcataatt cta           653
```

<210> SEQ ID NO 21
<211> LENGTH: 662
<212> TYPE: DNA
<213> ORGANISM: Artificial Sequence
<220> FEATURE:
<223> OTHER INFORMATION: nucleotide sequence encoding m909 light chain

<400> SEQUENCE: 21

```
ggcctcttct gagctgactc aggaccctgc tgtgtctgtg gccttgggac agacagtcag      60
gatcacctgc caaggagaca gcctcagaag caactatgca aactggtacc agcagaagcc    120
aggacaggcc cctgtacttg tcatctatgg tcaaaacaac cggccctcag ggatcccaga    180
```

```
ccgattctct ggctccagct caggaaacac agcttccttg accatcactg gggctcaggc      240
ggcagatgag gctgactatt actgtgactc ccgggtcagc actggtaacc atgtggtatt      300
cggcggaggg accaagctga ccgtcctagg tcagcccaag gctgccccct cggtcactct      360
gttcccgccc tcctctgagg agcttcaagc caacaaggcc acactggtgt gtctcataag      420
tgacttctac ccgggagccg tgacagtggc ctggaaggca gatagcagcc ccgtcaaggc      480
gggagtggag accaccacac cctccaaaca aagcaacaac aagtacgcgg ccagcagcta      540
tctgagcctg acgcctgagc agtggaagtc ccacagaagc tacagctgcc aggtcacgca      600
tgaagggagc accgtggaga agacagtggc ccctacagaa tgttcataat tctagataat      660
ta                                                                    662
```

US 8,871,206 B2

ANTI-HUMAN FOLATE RECEPTOR BETA ANTIBODIES AND METHODS OF USE

CROSS-REFERENCE TO RELATED APPLICATIONS

This application is a continuation-in-part of International Application No. PCT/US2011/050943, filed Sep. 9, 2011, which claims priority to U.S. Provisional Application Ser. No. 61/381,340, filed on Sep. 9, 2010, all of which are incorporated by reference in their entirety.

TECHNICAL FIELD

This invention relates to anti-folate receptor beta (FRβ) antibodies, and more particularly to human monoclonal antibodies, or antigen-binding fragments thereof, that specifically bind human FRβ and methods of using such antibodies or antigen binding fragments thereof to reduce the number of FRβ positive cells in subjects.

BACKGROUND

Folic acid is a vitamin required for the synthesis of nucleotide bases and is essential for the proliferation of all cells. Folates also are required for production of S-adenosylmethionine, the common substrate used in methylation of DNA, histones, G proteins, and many metabolic building blocks (see Kim, *J Nutr* 135:2703-2709 (2005); Loenen, *Biochem Soc Trans* 34:330-333 (2006)). Almost all cells take in folic acid via the reduced folate carrier or proton coupled folate transporter (see Matherly and Goldman, *Vitam Horm* 66:403-456 (2003)). Some cells, however, also express a folate receptor (FR) that binds folic acid ~100,000 times tighter than the aforementioned transporters, and carries bound folates into cells by receptor-mediated endocytosis (see Nakashima-Matsushita et al., *Arth Rheum* 42:1609-1616 (1999); Turk et al., *Arthritis Rheumatoid* 46:1947-1955 (2002)). There are four members of the FR family: FRα, FRβ, FRγ and FRδ (see Elnakat and Ratnam, *Adv Drug Deliv Rev* 56:1067-1084 (2004)). Different isoforms of the FR are used by certain cancer cells, activated macrophages, and the proximal tubule cells of the kidney to capture folates from their environment (see e.g., Nakashima-Matsushita et al. 1999, supra; and Turk et al. 2002, supra). A need exists for reagents and methods for differential targeting of the folate receptors for treatment of disease.

SUMMARY

This document is based on, inter alia, the identification of a human monoclonal antibody that specifically binds FRβ. Such an antibody or an antigen binding fragment thereof can be used to reduce the number of FRβ positive cells in a subject, and is useful for treating inflammatory disorders and cancers that express cell surface FRβ. The antibody described herein is particularly useful for treating human subjects as it is fully human, with reduced risk for inducing immune responses and side effects compared with murine, chimeric, or humanized antibodies.

In one aspect, this document features an isolated human monoclonal antibody, or an antigen-binding fragment thereof (e.g., Fab, a F(ab')$_2$ fragment, or a single chain antibody fragment (scFv)) that specifically binds human folate receptor beta (FRβ). The antibody or fragment can include a heavy chain variable region (V$_H$) complementarity determining region (CDR) 1 comprising the amino acid sequence set forth in SEQ ID NO:1; a V$_H$ CDR2 comprising the amino acid sequence set forth in SEQ ID NO:2; a V$_H$ CDR3 comprising the amino acid sequence set forth in SEQ ID NO:3; a light chain variable region (V$_L$) CDR1 comprising the amino acid sequence set forth in SEQ ID NO:4; a V$_L$ CDR2 comprising the amino acid sequence set forth in SEQ ID NO:5; and a V$_L$ CDR3 comprising the amino acid sequence set forth in SEQ ID NO:6. The antibody or fragment can include one or more framework regions in SEQ ID NO: 7 and SEQ ID NO:8. The antibody or fragment can have the amino acid sequence set forth in SEQ ID NO:10 or SEQ ID NO:11. The antibody or fragment can have the amino acid sequence set forth in SEQ ID NO:7 or SEQ ID NO:8. The antibody or fragment can bind to cell surface FRβ. The antibody can be an IgG$_1$ antibody. The antibody or fragment can induce antibody-dependent cell-mediated cytotoxicity (ADCC) of FRβ expressing target cells. In some embodiments, the antibody or fragment is de-fucosylated. In some embodiments, the antibody or fragment does not detectably bind to human folate receptor gamma (FRγ) or human folate receptor delta (FRδ).

In another aspect, this document features an isolated human monoclonal antibody, or an antigen-binding fragment thereof (e.g., Fab, a F(ab')$_2$ fragment, or a scFv) that specifically binds human FRβ. The antibody or fragment can include a V$_H$ CDR 1 comprising the amino acid sequence set forth in SEQ ID NO:1; a V$_H$ CDR2 comprising the amino acid sequence set forth in SEQ ID NO:2; a V$_H$ CDR3 comprising the amino acid sequence set forth in SEQ ID NO:3; a V$_L$ CDR1 comprising the amino acid sequence set forth in SEQ ID NO:14; a V$_L$ CDR2 comprising the amino acid sequence set forth in SEQ ID NO:15; and a V$_L$ CDR3 comprising the amino acid sequence set forth in SEQ ID NO:16. The antibody or fragment can include one or more framework regions in SEQ ID NO: 7 and SEQ ID NO: 17. The antibody or fragment can have the amino acid sequence set forth in SEQ ID NO:10 or SEQ ID NO:18. The antibody or fragment can have the amino acid sequence set forth in SEQ ID NO:7 or SEQ ID NO:17. The antibody or fragment can bind to cell surface FRβ. The antibody can be an IgG$_1$ antibody. The antibody or fragment can induce ADCC of FRβ expressing target cells. In some embodiments, the antibody or fragment is de-fucosylated. In some embodiments, the antibody or fragment does not detectably bind to human FRγ or human FRδ.

This document also features an isolated human monoclonal antibody, or an antigen-binding fragment thereof (e.g., Fab, a F(ab')$_2$ fragment, or a scFv) that specifically binds human FRβ. The antibody or fragment contains a V$_H$ CDR 1 comprising the amino acid sequence set forth in SEQ ID NO:1; a V$_H$ CDR2 comprising the amino acid sequence set forth in SEQ ID NO:2; and a V$_H$ CDR3 comprising the amino acid sequence set forth in SEQ ID NO:3. The antibody or fragment has one or more properties selected from the group consisting of: (a) the antibody or fragment does not detectably bind to human folate receptor alpha (FRα); (b) the antibody or fragment binds to human macrophages but not to mouse macrophages; (c) the antibody or fragment has a binding affinity (EC$_{50}$) of 20 nM; (d) the antibody or fragment has a dissociation constant (Kd) of 6.39 nM; and (e) the antibody mediates ADCC of FRβ-expressing target cells. In some embodiments, the antibody or fragment does not detectably bind to human FRγ or human FRδ.

This document also features an isolated heavy chain of an antibody, or antigen binding fragment of an antibody, that specifically binds human FRβ. The isolated heavy chain comprises a V$_H$ CDR 1 comprising the amino acid sequence set forth in SEQ ID NO:1; a V$_H$ CDR2 comprising the amino acid sequence set forth in SEQ ID NO:2; and a $V_H$ CDR3 comprising the amino acid sequence set forth in SEQ ID NO:3, wherein the antibody or fragment has one or more properties selected from the group consisting of: (a) the antibody or fragment does not detectably bind to human FRα; (b) the antibody or fragment binds to human macrophages but not to mouse macrophages; (c) the antibody or fragment has a binding affinity ($EC_{50}$) of 20 nM; (d) the antibody or fragment has a dissociation constant (Kd) of 6.393 nM; and (e) the ADCC of FRβ-expressing target cells. In some embodiments, the antibody or fragment does not detectably bind to human FRγ or human FRδ.

An antibody or fragment described herein can be conjugated with a pharmaceutical agent (e.g., a chemotherapeutic) or a liposome (e.g., a liposome including a pharmaceutical agent), linked to a toxin (e.g., covalently linked to the toxin) or a detectable moiety. The detectable moiety can be selected from the group consisting of a fluorescent moiety, a luminescent moiety, a radioactive moiety, a CT contrast agent, an MRI contrast agent, and biotin.

This document also features compositions including any of the antibodies or fragments described herein and a pharmaceutically acceptable carrier, and methods of using such compositions. For example, a composition can be used in a method of treating a patient having an inflammatory disorder (e.g., atherosclerosis, ischemia/reperfusion injury, transplantation rejection, vasculitis, inflammatory osteoarthritis, glomerulonephritis, restenosis, systemic sclerosis, fibromyalgia, sarcoidosis, or an autoimmune disease such as rheumatoid arthritis, systemic lupus erythematosus (SLE), ulcerative colitis, psoriasis, Type 1 diabetes, Crohn's disease, multiple sclerosis, and Sjogren's disease). The method can include administering to the patient an amount of a composition effective to reduce the number of FRβ positive macrophages and monocytes in the patient.

A composition described herein also can be used in a method of treating a patient having a cancer expressing cell-surface FRβ. The method can include administering to the patient, an amount of the composition effective to reduce the number of FRβ expressing cancer cells in the patient. The cancer can be a myeloid cancer (e.g., acute myeloid leukemia or chronic myeloid leukemia), multiple myeloma, or a solid FRβ expressing cancer (e.g., a non-epithelial malignancy).

This document also features a method of depleting activated macrophages from a human subject. The method includes administering to the subject a human monoclonal antibody, or antigen-binding fragment thereof, that specifically binds human FRβ, in an amount effective to reduce the number of activated macrophages in the subject.

In any of the methods described herein, the antibody or fragment thereof can induce ADCC of FRβ expressing target cells. In some embodiments, the antibody or fragment is de-fucosylated.

In any of the methods described herein, the antibody or fragment can induce opsonization-mediated clearance of FRβ expressing target cells.

In any of the methods described herein, the antibody or fragment can induce complement-mediated lysis of FRβ expressing target cells.

This document also features a nucleic acid that includes first and second segments, the first segment encoding a scFv fragment of a human monoclonal antibody that specifically binds human FRβ, and the second segment encoding at least the intracellular domain of a T cell signaling polypeptide. The T cell signaling polypeptide is a CD3 zeta chain or FcRγ chain. The nucleic acid further can include a third segment encoding at least the intracellular domain of a costimulatory polypeptide (e.g., a costimulatory polypeptide selected from the group consisting of CD28, CD40L, CD134, CD137, and PD-1). In addition, this document features cells that include any such nucleic acids. The cells can be T cells (e.g., cytotoxic T cells, CD8+ T cells, or CD4+ T cells). The T cells can produce at least one cytokine or lymphokine (e.g., interferon-γ (IFN-γ)).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1 is a depiction of the amino acid sequence of the full-length, unprocessed human FRβ protein (SEQ ID NO:9). A fragment of the full-length protein containing residues 22 to 236 was used to produce recombinant FRβ.

FIG. 2A is a depiction of the amino acid sequence of the m909 Fab heavy chain sequence (SEQ ID NO:7) and FIG. 2B is a depiction of the amino acid sequence of the m909 Fab light chain lambda sequence (SEQ ID NO:17). In each of the sequences, the framework regions are italicized, the CDRs are underlined, and the constant region is in lowercase, non-italicized text. By convention, numbering for framework regions 1-4 (FR1-FR4) is consecutive from the N-terminus, with FR1 being the most N-terminal sequence (not shown). By convention, numbering for CDR2 (CDRs 1-3) is also consecutive from the N-terminus, with CDR1 being the most N-terminal (not shown).

FIG. 6A contains four one-dimensional FFC histograms of control FITC-isotype IgG1 binding to CHO-hFRβ (a) or FITC-human anti-human FRβ IgG1 binding to CHO-hFRβ cells (b), KB cells (c), or CHO-K1 cells. FIG. 6B is a line graph showing the concentration of fluorescent intensity vs. human anti-human FRβ IgG1.

DETAILED DESCRIPTION

Figure 3:
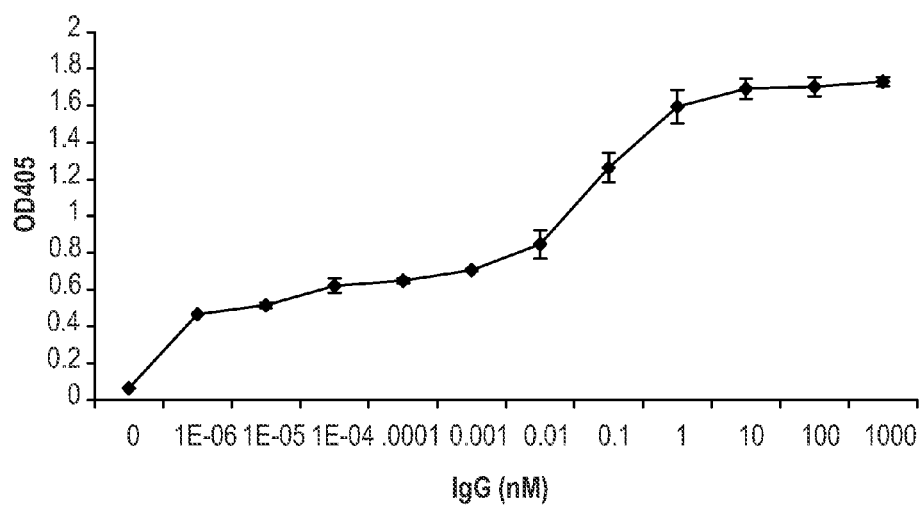
FIG. 3 is a graph showing the binding of m909 IgG to FRβ.

In general, this document provides human anti-human FRβ monoclonal antibodies or antigen-binding fragments thereof, as well as methods of using such antibodies or fragments thereof to treat, detect, or monitor an inflammatory disorder or a cancer expressing FRβ in a patient (e.g., a human patient). The term "FRβ" as used herein refers to human folate receptor beta. The amino acid sequence of human FRβ can be found in FIG. 1 (SEQ ID NO:9) and in GenBank under Accession No. NP_001107007. FRβ is a differential marker on the surface of myelomonocytic lineage cells. In normal tissues, FRβ is expressed in placenta, myelomonocytic lineage cells (e.g., monocytes and macrophages), and mature neutrophils. FRβ, however, does not bind folic acid on quiescent macrophages until the myeloid cell becomes activated. FRβ is consistently detected in multiple myeloma cells, chronic myeloid leukemia (CML) cells, and in 70% of acute myeloid leukemia (AML) cells. See, for example, Nakashima-Matsushita et al., 1999, supra; and Ross et al., *Contrast Media Mol Imaging* 2:72-81 (1999). FRβ also has been detected by RT-PCR in solid tumors (e.g., carcinomas from colon, kidney, breast, ovary, uterus, or lung; squamous cell carcinomas of the head and neck; and malignancies of non-epithelial origin such as sarcomas, lymphomas, fibrous histiocytomas, ovarian granulosa cell tumor, astrocytoma, meningiomas, and Wilms' tumor). See, for example, Ross et al., *Cancer*, 73:2432-43 (1994).

In monocytes and macrophage-lineage cells, FRβ expression is increased upon activation. For example, FRβ is expressed and functional in synovial macrophages in rheumatoid arthritis patients. Furthermore, γ-scintigraphy images of patients with a variety of inflammatory disorders (e.g., rheumatoid arthritis, Crohn's disease, ischemic bowel disease, Sjogren's syndrome, localized infections, atherosclerosis, and organ transplant rejection) show uptake of a folate-targeted $^{99m}$Tc imaging agent (EC20) at sites of inflammation (see Low et al., *Acc Chem Res.* 41(1):120-9 (2008); Matteson et al., *Clin Exp Rheumatol* 27:253-259 (2009); and Ayala-Lopez et al., *J Nuc Med*, 51:768-774 (2010)). These findings indicate expression of FRβ in activated macrophages and monocytes.

The antibodies and antigen binding fragments described herein specifically bind FRβ, and do not detectably bind FRα. In some embodiments, the antibodies and antigen binding fragments described herein also do not detectably bind FRγ and/or FRδ. FRα is expressed on the apical surfaces of a few epithelial cell types (primarily proximal tubules of the kidneys and alveolar epithelial cells of the lungs) and is upregulated on a variety of epithelial-derived tumors (see Weitman et al., *Cancer Res* 52:6708-6711 (1992); Salazar and Ratnam, *Cancer Mestastasis Rev* 26:141-152 (2007); and Leamon and Jackman, *Vitam Horm* 79:203-233 (2008)). FRγ is rarely expressed and difficult to detect in vivo. FRδ is expressed on regulatory T cells, where it exhibits only very low affinity for folic acid. As such, the antibodies and antigen binding fragments described herein, which specifically bind FRβ, can be used for depleting activated macrophages, treating inflammatory disorders, and treating cancers that express FRβ.

Human Anti-Human FRβ Antibodies

This document features fully human monoclonal antibodies (mAb), or antigen-binding fragments thereof, that specifically bind human FRβ. As used herein, the term "antibody" refers to a protein that generally comprises heavy chain polypeptides and light chain polypeptides. IgG, IgD, and IgE antibodies comprise two heavy chain polypeptides and two light chain polypeptides. IgA antibodies comprise two or four of each chain and IgM generally comprise 10 of each chain. Single domain antibodies having one heavy chain and one light chain and heavy chain antibodies devoid of light chains are also contemplated. A given antibody comprises one of five types of heavy chains, called alpha (1 or 2), delta, epsilon, gamma (1, 2, 3, or 4), and mu, the categorization of which is based on the amino acid sequence of the heavy chain constant region. These different types of heavy chains give rise to five classes of antibodies, IgA (including IgA1 and IgA2), IgD, IgE, IgG (IgG1, IgG2, IgG3 and IgG4) and IgM, respectively.

In an IgG antibody, the heavy chain includes a "hinge region", "$C_H1$ region", "$C_H2$ region", "$C_H3$ region" each of which refers to a different region of the heavy chain constant region. The hinge region is located between the $C_H1$ region and $C_H2$ region, and links the Fab region to the Fc region. Thus, N terminal to C terminal, the regions are in the order $C_H1$, hinge, $C_H2$, and $C_H3$. In the μ heavy chain constant regions of IgM antibodies, there is an extra C-terminal region, the $C_H4$ region. The antibodies and fragments of this document can contain all or some of the regions of the heavy chain constant regions. Thus, they can contain all or part or the hinge region, and/or all or part of the $C_H1$ region, and/or all or part of the $C_H2$ region, and/or all or part of the $C_H3$ region, and/or all or part of the $C_H4$ region. Moreover, any of these regions, or parts of regions, can in any particular antibody or fragment, be derived from one, two, three, four, five, six, seven, eight, or nine different constant region classes or subclasses (γ1, 2, 3, or 4, α1 or 2, ε, μ, and δ).

Antibodies and antigen binding fragments described herein can be of any class and have the corresponding heavy chain constant region. A given antibody also comprises one of two types of light chains, called kappa or lambda, the categorization of which is based on the amino acid sequence of the light chain constant regions. Antibodies and antigen binding fragments described herein can have either class of light chain.

Fully human monoclonal antibodies that specifically bind to FRβ can be produced, e.g., using in vitro-primed human splenocytes as described by Boerner et al., *J. Immunol.*, 147, 86-95 (1991), or repertoire cloning as described by Persson et al., *Proc. Nat. Acad. Sci. USA*, 88: 2432-2436 (1991); Huang and Stollar, *J. Immunol. Methods* 141, 227-236 (1991); or U.S. Pat. No. 5,798,230. Large nonimmunized or immunized human phage display libraries also can be used to isolate high affinity antibodies using standard phage technology (see, e.g., Hoogenboom et al., *Immunotechnology* 4:1-20 (1998); Hoogenboom et al., *Immunol Today* 2:371-8 (2000); and U.S. Patent Publication No. 2003-0232333). In addition, a TransChromo mouse carrying human immunoglobulin loci, including all the subclasses of IgGs (IgG1-G4), can be used to prepare human monoclonal antibodies. See, Ischida et al., *Cloning Stem Cells* 4(1):91-102 (2002).

"Antigen binding fragment" of an antibody as the term is used herein refers to an antigen binding molecule that is not a complete antibody as defined above, but that still retains at least one antigen binding site. Thus, in one embodiment, an antigen binding fragment is a fragment of an antibody that binds to FRβ. Antibody fragments often include a cleaved portion of a whole antibody, although the term is not limited to such cleaved fragments. Antigen binding fragments can include, for example, a Fab, F(ab')$_2$, Fv, and single chain Fv (scFv) fragment. An scFv fragment is a single polypeptide chain that includes both the heavy and light chain variable regions of the antibody from which the scFv is derived. Other suitable antibodies or antigen binding fragments include linear antibodies, multispecific antibody fragments such as bispecific, trispecific, and multispecific antibodies (e.g., diabodies (Poljak *Structure* 2(12):1121-1123 (1994); Hudson et al., *J. Immunol. Methods* 23(1-2):177-189 (1994)), triabodies, tetrabodies), minibodies, chelating recombinant antibodies, intrabodies (Huston et al., *Hum. Antibodies* 10(3-4):127-142 (2001); Wheeler et al., *Mol. Ther.* 8(3):355-366 (2003); Stocks *Drug Discov. Today* 9(22): 960-966 (2004)), nanobodies, small modular immunopharmaceuticals (SMIP), binding-domain immunoglobulin fusion proteins, camelid antibodies, camelized antibodies, and V$_{HH}$ containing antibodies.

A human anti-human FRβ mAb or antigen-binding fragment thereof described herein specifically binds to human FRβ, but does not detectably bind to FRα. In some embodiments, the anti-human FRβ mAb or antigen-binding fragment thereof also does not detectably bind to FRγ and/or FRδ. Binding specificity can be assessed as described herein. For example, binding specificity of an antibody or antigen binding fragment thereof can be assessed using recombinantly produced FR or cells expressing a particular FR on their cell surface and techniques such as enzyme linked immunosorbent assay (ELISA) or flow cytometry. As described herein, human anti-human FRβ mAb can bind cell surface FRβ, and antigen binding fragments of human anti-human FRβ mAb (e.g., Fab or scFv) can bind cell surface FRβ mAb when bivalent. Human anti-human FRβ mAb can bind to human macrophages but not to mouse macrophages. As described herein, in Fab format, m909 bound to recombinant FRβ with high (nM) affinity (EC$_{50}$=20 nM). In an IgG1 format, m909 has high (subnanomolar) avidity in vitro and specifically binds to cell surface FRβ. As described in Example 3, the human anti-human FRβ mAb has a dissociation constant (Kd) of 6.393 nM.

In some embodiments, an antibody or antigen binding fragment thereof described herein contains a heavy chain variable region (V$_H$) complementarity determining region (CDR) 1 having the amino acid sequence set forth in SEQ ID NO:1 [GYTFTSYA], a V$_H$ CDR2 having the amino acid sequence set forth in SEQ ID NO:2 [KYSQKFQ]; and a V$_H$ CDR3 having the amino acid sequence set forth in SEQ ID NO:3 [ARDISYGSFDYW]. Alternatively, or in addition, the antibody or antigen binding fragment thereof described herein contains a light chain variable region (V$_L$) CDR1 having the amino acid sequence set forth in SEQ ID NO:4 [NLRSYY]; a V$_L$ CDR2 having the amino acid sequence set forth in SEQ ID NO:5 [GKN]; and a V$_L$ CDR3 having the amino acid sequence set forth in SEQ ID NO:6 [HSRKSRGNHLLF].

In some embodiments, the antibody or fragment described herein can include one or more framework regions italicized in the following amino acid sequence: [*EVQLVQSGAE-VKKPGASVKVSCKAS* GYTFTSYAMH *WVRQAPGQRLEWMG* WINAG NGNT *KYSQKFQGRVTITRDTSASTAYMELSSLRSEDTAVYYC* ARDISYGSFDYW*GQG TLVTVSS*astkgpsvfplapssksstggtaalgclvkdyfpepvtvswnsgaltsgvhtfpavlqssglyslssvvtvpsssl gtqtyicnvnhkpsntkvdkkvepkscdktsgqag] (SEQ ID NO:7, heavy chain sequence; constant region in lower class letters)). Alternatively, or in addition, the antibody or fragment described herein can include one or more framework regions italicized in the following amino acid sequence: [*SSELTQD-PAVSVALGQTVRITCQGD* NLRSYYA*SWYRQKSGQAPVLVIY* GKNNRPSGI PDRFSGSSSGNTASLTITAAQAEDEADYYC HSRKSRGNHLLF*GGGTKLTVL*gqpkaapsv tlfppsseelqankatlvclisdfypgavt-vakadsspvkagvetttpskqsnnkyaassylsltpeqwkshrsyscqvthegs tvektvaptecs] (SEQ ID NO:8, lambda light chain sequence; constant region in lower case letters).

In some embodiments, the antibody or antigen binding fragment thereof comprises the heavy chain variable region (V$_H$) amino acid sequence set forth in SEQ ID NO:10 [EVQLVQSGAEVKKPGASVKVSCKASGYTFTSYAMHWVRQAPGQRLEWMGWI NAGNGNTKYSQKFQGRVTITRDTSASTAYMELSSLRSEDTAVYYCARDISYGSF DYWGQGTLVTVSS]. Alternatively, or in addition, the antibody or antigen binding fragment thereof comprises the light chain variable region amino acid (V$_1$) amino acid sequence set forth in SEQ ID NO:11 [SSELTQDPAVSVALGQTVRITCQGDNL-RSYYASWYRQKSGQAPVLVIYGKNNR PSGIPDRF-SGSSSGNTASLTITAAQAEDEADYYCH-SRKSRGNHLLFGGGTKLTVL]. In some embodiments, an antibody or fragment thereof comprising such sequences is designated m923 and specifically binds to human FRβ.

In some embodiments, the antibody or fragment described herein can include the following heavy chain amino acid sequence: [EVQLVQSGAEVKKPGASVKVSCKASGYTFTSYAMHWVRQAPGQRLEWMGWI NAGNGNTKYSQKFQGRVTITRDTSASTAYMELSSLRSEDTAVYYCARDISYGSF DYWGQGTLVTVSSASTKGPSVF-PLAPSSKSTSGGTAALGCLVKDYFPEPVTVSW NSGALTSGVHTFPAVLQSSGLYSLSSV-VTVPSSSLGTQTYICNVNHKPSNTKVDK KVEPKSCDKTSGQAG] (SEQ ID NO:7). Alternatively, or in addition, the antibody or fragment described herein can include the following light chain amino acid sequence: [SSELTQD-PAVSVALGQTVRITCQGDNLRSYYASW-YRQKSGQAPVLVIYGKNNR PSGIPDRFSGSSSGN-TASLTITAAQAEDEADYYCHSRKSRGNHLLFGGGTK-LTVL GQPKAAPSVTLFPPSSEELQANKATLV-CLISDFYPGAVTVAKADSSPVKAGVETT TPSKQSNN-KYAASSYLSLTPEQWKSHRSYSCQV-THEGSTVEKTVAPTECS] (SEQ ID NO:8).

In some embodiments, the antibody or antigen binding fragment thereof described herein contains a heavy chain variable region (V$_H$) complementarity determining region (CDR) 1 having the amino acid sequence set forth in SEQ ID NO:1 [GYTFTSYA], a V$_H$ CDR2 having the amino acid sequence set forth in SEQ ID NO:2 [KYSQKFQ]; and a V$_H$ CDR3 having the amino acid sequence set forth in SEQ ID NO:3 [ARDISYGSFDYW]. Alternatively, or in addition, the antibody or antigen binding fragment thereof described herein contains a light chain variable region (V$_L$) CDR1 having the amino acid sequence set forth in SEQ ID NO:14 [SLRSNY]; a V$_L$ CDR2 having the amino acid sequence set forth in SEQ ID NO:15 [GQN]; and a V$_L$ CDR3 having the amino acid sequence set forth in SEQ ID NO:16 [DSRVST-GNHVVF].

In some embodiments, an antibody or fragment described herein can include one or more framework regions italicized in the following amino acid sequence: [EVQLVQSGAE- VKKPGASVKVSCKAS
GYTFTSYAMHWVRQAPGQRLEWMGWINAG NGNT
KYSQKFQGRVTITRDTSASTAYMELSSLRSEDTAVYYC
ARDISYGSFDYWGQG TLVTVSSastkgpsvfplapsskstsgg-
taalgclvkdyfpepvtvswnsgaltsgvhtfpavlqssglyslssvvtvpsssl
gtqtyicnvnhkpsntkvdkkvepkscdktsgqag] (SEQ ID NO:7, heavy chain sequence; constant region in lower case letters). Alternatively, or in addition, the antibody or fragment described herein can include one or more framework regions italicized in the following amino acid sequence: [SSELTQD-PAVSVALGQTVRITCQGD
SLRSNYANWYQQKPGQAPVLVIYGQNNRPSGI
PDRFSGSSSGNTASLTITGAQAADEADYYC
DSRVSTGNHVVFGGGTKLTVLgqpkaaps vtlfpps-seelqankatlvclisdfypgavt-
vakadsspvkagvetttpskqsnnkyaassylsltpeqwkshrsyscqvthe
gstvektvaptecs] (SEQ ID NO:17, lambda light chain sequence; constant region in lower case letters).

In some embodiments, the antibody or antigen binding fragment thereof comprises the $V_H$ amino acid sequence set forth in SEQ ID NO:10 [EVQLVQSGAEVKKPGAS-VKVSCKASGYTFTSYAMHWVRQAPGQR-LEWMGWINAGNG NTKYSQKFQGRVTITRDTSAS-TAYMELSSLRSEDTAVYYCARDISYGSFDYWGQGTL-VT VSS]. Alternatively, or in addition, the antibody or antigen binding fragment thereof comprises the $V_L$ amino acid sequence set forth in SEQ ID NO:18 [SSELTQDPAVSVAL-GQTVRITCQGDSLRSNYANWYQQK-PGQAPVLVIYGQNNRPSGIPD RFSGSSSGNTASLTIT-GAQAADEADYYCDSRVSTGNHVVFGGGTKLTVL]. In some embodiments, the antibody or antigen binding fragment thereof is designated m909.

In some embodiments, an antibody or fragment described herein can include the following heavy chain amino acid sequence: [EVQLVQSGAEVKKPGASVKVSCKASGYT-FTSYAMHWVRQAPGQRLEWMGWI NAGNGNT-KYSQKFQGRVTITRDTSASTAYMELSSL-RSEDTAVYYCARDISYGSF
DYWGQGTLVTVSSASTKGPSVF-PLAPSSKSTSGGTAALGCLVKDYFPEPVTVSW
NSGALTSGVHTFPAVLQSSGLYSLSSV-VTVPSSSLGTQTYICNVNHKPSNTKVDK KVEPKSCD-KTSGQAG] (SEQ ID NO:7). Alternatively, or in addition, the antibody or fragment described herein can include the following light chain amino acid sequence: [SSELTQD-PAVSVALGQTVRITCQGDSLRSNYANW-YQQKPGQAPVLVIYGQNNR PSGIPDRFSGSSSGN-TASLTITGAQAADEADYYCDSRVSTGNHVVFGGGTK-LTVL GQPKAAPSVTLFPPSSEELQANKATLV-CLISDFYPGAVTVAKADSSPVKAGVETT TPSKQSNN-KYAASSYLSLTPEQWKSHRSYSCQV-THEGSTVEKTVAPTECS] (SEQ ID NO:17).

It is understood that antibodies and antigen binding fragments described above, whether specified in terms of heavy and light chain components, or heavy or light chain components, can have any of the functional properties and activities described herein.

In some embodiments, the full length heavy or light chain, variable region, CDR, framework region, or constant region of an antibody or antigen binding fragment described herein can have at least 80% sequence identity (e.g., at least 85%, 90%, 95%, 97%, 98%, 99%, or 100% sequence identity) to the corresponding amino acid sequence set forth in any one of SEQ ID NOs:1-8, 10, 11, and 14-18. The percent identity between a particular amino acid sequence and the amino acid sequence set forth in any one of SEQ ID NOs:1-8, 10, 11, and 14-18 can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site or the U.S. government's National Center for Biotechnology Information web site. Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: —i is set to a file containing the first amino acid sequence to be compared (e.g., C:\seq1.txt); —j is set to a file containing the second amino acid sequence to be compared (e.g., C:\seq2.txt); —p is set to blastp; —o is set to any desired file name (e.g., C:\output.txt); and all other options are left at their default setting. For example, the following command can be used to generate an output file containing a comparison will present those regions of homology as aligned sequences. If the two compared sequences do not share homology, then the designated output file will not present aligned sequences. Similar procedures can be followed for nucleic acid sequences except that blastn is used.

Once aligned, the number of matches is determined by counting the number of positions where an identical amino acid residue is presented in both sequences. The percent identity is determined by dividing the number of matches by the length of the amino acid sequence in SEQ ID NOs:1-8, 10, 11, or 14-18, followed by multiplying the resulting value by 100.

It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode the amino acid sequences set forth in SEQ ID NOs: 1-8, 10, 11, and 14-18. The degeneracy of the genetic code is well known to the art; i.e., for many amino acids, there is more than one nucleotide triplet that serves as the codon for the amino acid. The nucleotide sequence encoding the amino acid sequence of SEQ ID NO:7 is set forth in SEQ ID NO: 19. The nucleotide sequence encoding the amino acid sequence of SEQ ID NO:8 is set forth in SEQ ID NO: 20. The nucleotide sequence encoding the amino acid sequence of SEQ ID NO: 17 is set forth in SEQ ID NO:21. In some embodiments, a heavy or light chain of an antibody is encoded by a nucleic acid having at least 80% sequence identity (e.g., at least 85%, 90%, 95%, 97%, 98%, 99%, or 100% sequence identity) to the nucleotide sequences set forth in SEQ ID NOs. 19-21. Sequence identity is calculated as described above for protein sequences except that blastn is used.

In some embodiments, an antibody or antigen binding fragment thereof described herein induces antibody-dependent cell-mediated cytotoxicity (ADCC) of FRβ expressing target cells. Suitable antigen binding fragments that induce ADCC have a functional Fc region, i.e., an Fc region that can bind to an Fc receptor on an ADCC effector cell. The antibodies and antigen binding fragments thereof can bind to IgG Fc binding receptors (FcγR) receptors I, II and III (CD64, CD32, and CD16) in order to mediate the functional activities described herein. In some embodiments, binding to a FcγR (e.g., FcγR III) can be enhanced by removing fucose residues from and/or by increasing galactosylation of the glycan present on the Fc portion of an $IgG_1$. See, for example, Houdes et al., *Molecular & Cellular Proteomics* 9:1716-1728 (2010); Kubota et al., *Cancer Sci.,* 100: 1566-1572 (2009); Malphettes et al., *Biotechnol. Bioeng.,* 106:774-783 (2010); and Raju, *Curr. Opin. Immunol.,* 20:471-478 (2008). Defucosylated antibodies can be produced using, for example, cells with reduced expression of the GDP-4,6-dehydratase gene (e.g., from a mutation such as that in Chinese hamster ovary (CHO) Lec13 cells or from a small interfering RNA against the GDP-4,6-dehydratase gene), cells in which the α-1,6-fucosyltransferase (FUT8) has been knocked out or expression reduced (e.g., using a small interfering RNA (siRNA) against the FUT8 gene), cells co-expressing β-1,4-N-acetylglucosaminyltransferase III (GnT-III) and Golgi α mannosidase II (ManII), or cells expressing GDP-6-deoxy-D-lyxo-4-hexylose reductase (RMD). See, Ishiguro et al., *Cancer Sci.*, pages 1-7, July, 2010; and von Horsten, *Glycobiology*, published online Jul. 23, 2010. FcγR binding also can be enhanced by mutating relevant amino acids in the heavy chain constant regions comprising the Fc region (e.g., the hinge region, the $C_H2$ region, or the $C_H3$ region). See, for example, Natsume et al., *Drug Des. Develop. Ther.*, 3:7-16 (2009). In some embodiments, an antibody or fragment thereof can induce opsonization-mediated clearance and/or induce complement-mediated lysis of FRβ expressing target cells. ADCC can be assessed in vitro using a lactate dehydrogenase (LDH) release assay or chromium-51 release assay.

This document also provides antibodies that bind to particular epitopes of FRβ that contain, for example, at least three amino acids of human FRβ (FIG. 1, SEQ ID NO: 9). For example, an epitope can contain 3 to 30 such as 5 to 25, 7 to 23, 10 to 20, or 13 to 18 amino acids of human FRβ). For example, an epitope can contain 3, 4, 5, 6, 7, 8, 9, 10, 11, 12, 13, 14, 15, 16, 17, 18, 19, 20, 21, 22, 23, 24, 25, 26, 27, 28, 29, or 30 amino acids of human FRβ. The epitope can be in the N-terminal half (i.e., residues 1 to 127 of SEQ ID NO: 9) or the C-terminal half of human FRβ (i.e., residues 128 to 255 of SEQ ID NO:9).

An antibody or antigen binding fragment described herein can be conjugated or linked, either covalently or noncovalently, to a variety of molecules, including pharmaceutical agents, liposomes, oligonucleotides (e.g., small interfering RNA (siRNA)), toxins, detectable moieties, or biological molecules (e.g., a cytokine such as an interleukin (IL) 2, IL4, IL 12, 13 or 15; interferon (IFN) α, IFN β, or IFN γ) using methods known in the art. Conjugating or linking such molecules to an antibody or antigen binding fragment described herein allows the molecule to be targeted specifically to FRβ. As such, molecules can be delivered to the desired site while minimizing toxicity.

For example, an antibody or antigen binding fragment can be conjugated with a pharmaceutical agent such as a chemotherapeutic (e.g., cisplatin, carboplatin, procarbazine, mechlorethamine, cyclophosphamide, camptothecin, adriamycin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, transplatinum, 5-fluorouracil, vincristin, vinblastin, methotrexate, or an analog of any of the aforementioned). An antibody or antigen binding fragment also can be conjugated with an anti-inflammatory agent such as a glucocorticoid, nonsteroidal anti-inflammatory agent, phosphoinositide-3-kinase inhibitor (e.g., wortmannin or derivatives such as demethoxyviridin, PX-866, LY294002, and LY294002 RGDS (Arg-Gly-Asp-Ser)-conjugated prodrug SF1126, see, e.g., Maira et al., *Biochem. Soc. Trans.*, 37, 265-272 (2009)); NF-kappa-B inhibitor, I-kappa-B kinase inhibitor, mTOR (mammalian target of rapamycin) inhibitor (e.g., rapamycin, CCI-779, RAD001, or AP23573, see Maira et al., supra), mitogen activated protein (MAP) kinase inhibitor (e.g., SB-203580 and VX-745, see Brown et al., *J. Inflammation*, 5:22 (2008), or a Janus kinase (JAK) inhibitor.

An antibody or antigen binding fragment also can be conjugated with a liposome. See, for example, the nanoliposomes of Low et al. (*Accounts of Chemical Research*, 41(1):120-129 (2008)) that are less than 100 nm in diameter and contain a portion of PEGylated lipids (i.e., a lipid linked to polyethylene glycol (PEG)). Liposomes can be loaded with a pharmaceutical agent using methods known in the art.

An antibody or antigen binding fragment described herein can be linked to a toxin such as *Pseudomonas* exotoxin A (PE), diphtheria toxin (DT), gelonin, saporin, ricin A, abrin, mistletoe lectin, modeccin, pokeweed antiviral protein (PAP), Bryodin 1, bouganin, or biologically active fragments thereof, to generate an immunotoxin. See, for example, Kreitman, *BioDrugs*, 23(1):1-13 (2009). PE and DT, and biologically active fragments thereof, are particularly useful. A biologically active fragment of PE can include, for example, amino acids 253-364 and 381-613 of PE as described by Hassan et al., *J Immunother.*, 23:473-9 (2000). A biologically active fragment of DT can include DT388 or DAB389, which contain the first 388 or 389 amino acids of DT. See, for example, Chaudhary et al., *Biochem Biophys Res Commun.*, 180:545-51 (1991). Such immunotoxins are useful for killing FRβ expressing cells (e.g., any of the cancer cells described herein) in vivo or in vitro.

An antibody or antigen binding fragment described herein can be linked to a detectable moiety. Suitable detectable moieties include, without limitation, radionuclides (e.g., radionuclides used for in vivo diagnostics such as $^{186}$Re, $^{188}$Re, $^{64}$Cu, $^{67}$Cu, $^{212}$Bi, $^{123}$I, $^{131}$I, $^{211}$At, $^{177}$Lu, $^{47}$Sc, $^{105}$Rh, $^{109}$Pd, $^{153}$Sm, $^{199}$Au, $^{99m}$Tc, $^{111}$In, $^{124}$I, $^{18}$F, $^{11}$C, $^{198}$Au, $^{75}$Br, $^{76}$Br, $^{77}$Br, $^{13}$N, $^{34m}$Cl, $^{38}$Cl, $^{52m}$Mn, $^{55}$Co, $^{62}$Cu, $^{68}$Ga, $^{72}$As, $^{76}$As, $^{72}$Se, $^{73}$Se, or $^{75}$Se; or radionuclides useful for in vitro experiments such as $^{125}$I, $^{35}$S, $^3$H, $^{32}$P, $^{33}$P, or $^{14}$C), fluorescent moieties (e.g., fluorescein, fluorescein isothiocyanate (FITC), PerCP, rhodamine, or phycoerythrin (PE)), luminescent moieties (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). Antibodies can be indirectly labeled by conjugation with biotin then detected with avidin or streptavidin labeled with a molecule described above. Methods of detecting or quantifying a detectable moiety depend on the nature of the moiety and are known in the art. Examples of detectors include, without limitation, x-ray film, radioactivity counters, scintillation counters, spectrophotometers, colorimeters, fluorometers, luminometers, and densitometers. Methods of attaching the radionuclide atoms (or larger molecules/chelates containing them) to an antibody or antigen binding fragment thereof are known in the art and can include incubating the antibody or fragment thereof with the radionuclide under conditions (e.g., pH, salt concentration, and/or temperature) which facilitate binding of the radionuclide atom or radionuclide atom-containing molecule or chelate to the antibody or antigen binding fragment (see, e.g., U.S. Pat. No. 6,001,329).

Other examples of detectable moieties that can be linked to an antibody or antigen binding fragment include imaging agents, such as MRI or computed tomography (CT) contrast agents. Non-limiting examples of MRI contrast agents include gadolinium and manganese chelates, iron salts, or gadolinium compounds such as gadodiamide (OMNISCAN®), gadobenic acid (MULTIHANCE®), gadopentetic acid (MAGNAVIST®), gadoteridol (PROHANCE®), gadofosveset (ABLAVAR®), gadoversetamide (OPTIMARK®), or gadoxetic acid (EOVIST®, known). Non-limiting examples of CT contrast agents include iodine based agents such as UROGRAFIN®, TELEBRIX®, GASTROGRAFIN®, OMNIPAQUE™, ULTRAVIST®, or VISIPAQUE™.

In some embodiments, a nucleic acid encoding an antibody or an antigen binding fragment such as an scFv fragment is included in a construct for producing a chimeric immune receptor. Chimeric immune receptors typically include an extracellular portion and an intracellular portion, where the extracellular portion is an antigen binding fragment (e.g., a scFv fragment) having binding affinity for human FRβ and the intracellular portion is at least the intracellular domain of a signaling polypeptide such as the CD3 zeta chain, FcRγ chain, or a kinase such as a Syk cytoplasmic phosphotyrosine kinase. A chimeric immune receptor further can include at least the intracellular domain of a costimulatory polypeptide such as the intracellular domain of CD28 or other costimulatory polypeptide such as OX40 (CD134), CD40L, PD-1, or 4-1BB (CD137). In some embodiments, a chimeric immune receptor includes an scFv fragment fused to the nonligand binding part of the extracellular and the entire transmembrane and intracellular domains of CD28, which is fused with the intracellular domain of FcRγ. Constructs encoding chimeric immune receptors can be introduced ex vivo (e.g., using a retroviral vector) into T cells (e.g., cytotoxic T cells, CD4+ T cells, or CD8+ T cells) from peripheral lymphocytes of a given patient, and the resulting engineered T cells containing the chimeric receptor can be re-introduced into the patient. The engineered T cells can produce at least one cytokine or lymphokine (e.g., IL2, IL3, IL4, IL5, IL6, IL9, IL10, IL12, or IFNγ). Upon binding of the engineered T cells to FRβ expressing target cells, the engineered T cells are activated and can kill the FRβ expressing target cells. See, for example, Eshhar in "Therapeutic Antibodies. Handbook of Experimental Pharmacology 181" Y. Chernajovsky, A. Nissim (eds.), 2008; and Pienert et al., *Immunotherapy*, 1(6): 905-912 (2009).

Methods of Using Antibodies

Typically, a human anti-human FRβ mAb or antigen binding fragment thereof is administered to a mammal such as a human patient that has been diagnosed with an inflammatory disorder or a cancer expressing cell surface FRβ. In some embodiments, engineered T cells containing a chimeric immune receptor (see above section) are administered to the human patient. Non-limiting examples of inflammatory disorders include atherosclerosis, ischemia/reperfusion injury, transplantation rejection, vasculitis such as Wegener's granulomatosus, inflammatory osteoarthritis, glomerulonephritis, restenosis, systemic sclerosis, fibromyalgia, sarcoidosis, and autoimmune diseases. Non-limiting examples of autoimmune diseases include rheumatoid arthritis, systemic lupus erythematosus (SLE), ulcerative colitis, psoriasis, Type 1 diabetes (insulin-dependent diabetes mellitus), Crohn's disease, multiple sclerosis, and Sjogren's disease. Inflammatory disorders also can include obstructive pulmonary diseases such as asthma or chronic obstructive pulmonary disease (COPD).

The antibodies or fragments described herein also can be administered to a subject suspected of having an inflammatory disorder. A subject "suspected of having an inflammatory disorder" is one having one or more signs of the disorder. Signs of such disorders are well-known to those of skill in the art and include, without limitation, redness, swelling (e.g., swollen joints), skin rashes, joint pain, joint pain, loss of joint function, fever, chills, fatigue, loss of energy, headaches, loss of appetite, muscle stiffness, insomnia, itchiness, stuffy nose, sneezing, coughing, or one or more neurologic symptoms such as weakness, paresthesias, paralysis, dizziness, seizures, or pain. Signs of diabetes include, without limitation, higher than normal frequency of urination, unusual thirst, extreme hunger, unusual weight loss, extreme fatigue, visual problems, and irritability.

Non-limiting examples of cancers expressing cell surface FRβ include myeloid cancers such as acute myeloid leukemia (AML) or chronic myeloid leukemia (CML), multiple myeloma, or a solid cancer containing FRβ expressing cells such as squamous cell carcinoma of the head and neck, or a malignancy of non-epithelial origin. Treatment of an inflammatory disorder or cancer can include reducing the severity of the disorder or slowing progression of the disorder.

A human anti-human FRβ mAb, or antigen binding fragment thereof, also can be administered prophylactically in subjects at risk for developing an inflammatory disorder to prevent development of symptoms of the disorder from occurring, delay onset of symptoms, or lessen the severity of subsequently developed disorder symptoms. A subject "at risk of developing an inflammatory disorder" refers to a subject with a family history of one or more inflammatory disorders (e.g., a genetic predisposition to one or more inflammatory disorders) or one exposed to one or more inflammation-inducing conditions. For example, a subject can have been exposed to a viral or bacterial superantigen such as, but not limited to, Staphylococcal enterotoxins (SEs), a *Streptococcus pyogenes* exotoxin (SPE), a *Staphylococcus aureus* toxic shock-syndrome toxin (TSST-1), a Streptococcal mitogenic exotoxin (SME) and a Streptococcal superantigen (SSA). An antibody or fragment thereof also can be administered to deplete activated macrophages from a human subject. In any case, an amount of the antibody or antigen binding fragment thereof effective to reduce the number of FRβ positive cells (e.g., macrophages and monocytes, or cancer cells) in the patient is administered. The number of FRβ positive cells can be determined by doing cell counts or using a folate-targeted imaging agent.

Methods described herein can include monitoring the patient to, for example, determine if the disorder is improving with treatment. Any method can be used to monitor an inflammatory disorder or cancer. For example, for rheumatoid arthritis patients, joint pain and/or stiffness, or bone erosion can be monitored in the patient. For cancer patients, tumor size, cell count, or cancer specific markers can be monitored.

Antibodies or antibody fragments described herein (with or without linked moieties) may be administered by any available route including, but not limited to, oral or parenteral routes of administration such as intravenous, intramuscular, intraperitoneal, subcutaneous, intrathecal, intraarterial, nasal, transdermal (e.g., as a patch), or pulmonary absorption. Antibodies or antibody fragments may include a delivery agent (e.g., a cationic polymer, peptide molecular transporter, surfactant, etc.) as a composition containing a pharmaceutically acceptable carrier. As used herein the term "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into pharmaceutical formulations as described herein.

A pharmaceutical composition is formulated to be compatible with its intended route of administration. Solutions or suspensions used for parenteral administration can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR® ELTM (BASF, Parsippany, N.J.) or phosphate buffered saline (PBS). In all cases, the composition should be sterile and should be fluid to the extent that easy syringability exists. Pharmaceutical formulations are ideally stable under the conditions of manufacture and storage and should be preserved against the contaminating action of microorganisms such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the antibody or antibody fragment in the required amount in an appropriate solvent with one or a combination of ingredients enumerated above, as required, followed by filtered sterilization. Generally, dispersions are prepared by incorporating the purified antibody or antibody fragment into a sterile vehicle which contains a basic dispersion medium and the required other ingredients from those enumerated above. In the case of sterile powders for the preparation of sterile injectable solutions, exemplary methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the antibody or antibody fragment can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the antibody or antibody fragment and a delivery agent are preferably delivered in the form of an aerosol spray from a pressured container or dispenser which contains a suitable propellant, e.g., a gas such as carbon dioxide, or a nebulizer. The present disclosure particularly contemplates delivery of the compositions using a nasal spray, inhaler, or other direct delivery to the upper and/or lower airway. According to certain embodiments, antibody or antibody fragment and a delivery agent are formulated as large porous particles for aerosol administration.

Systemic administration also can be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the purified polypeptide or protein and delivery agents are formulated into ointments, salves, gels, or creams as generally known in the art.

In certain embodiments, compositions are prepared with carriers that will protect the antibody or antibody fragment against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active antibody or antibody fragment calculated to produce the desired therapeutic effect in association with the required pharmaceutical carrier.

The antibody or antibody fragment can be administered at various intervals and over different periods of time as required. Those of ordinary skill in the art will appreciate that certain factors can influence the dosage and timing required to effectively treat a subject, including but not limited to the severity of the disease or disorder, previous treatments, the general health and/or age of the subject, and other diseases present. Generally, treatment of a subject with an antibody or antibody antigen-binding fragment as described herein can include a single treatment or, in many cases, can include a series of treatments. It is furthermore understood that appropriate doses may depend upon the potency of the antibody or antibody fragment and may optionally be tailored to the particular recipient, for example, through administration of increasing doses until a preselected desired response is achieved. It is understood that the specific dose level for any particular animal subject may depend upon a variety of factors including the activity of the specific polypeptide or protein employed, the age, body weight, general health, gender, and diet of the subject, the time of administration, the route of administration, the rate of excretion, any drug combination, and the degree of expression or activity to be modulated.

Pharmaceutical formulations as described herein can be included in a container, pack, or dispenser together with instructions for administration.

In some embodiments, an antibody or antigen binding fragment thereof is administered in combination with one or more pharmaceutical agents (e.g., an anti-inflammatory agent) or antibodies.

Articles of Manufacture

Antibodies or antigen binding fragments described herein that specifically bind FRβ can be combined with packaging material and sold as a kit for treating inflammatory disorders, treating a cancer expressing cell surface FRβ, or depleting activated macrophages from a subject. The articles of manufacture may combine one or more human anti-human FRβ antibodies or fragments thereof. In addition, the articles of manufacture may further include reagents such as secondary antibodies, buffers, indicator molecules, solid phases (e.g., beads), pharmaceutical agents, and/or other useful reagents for treating inflammatory disorders, treating cancer, or depleting activated macrophages from a subject. Instructions describing how the various reagents are effective for treating inflammatory disorders, treating cancer, or depleting activated macrophages from a subject also may be included in such kits.

Certain embodiments of methods and compositions provided herein are further illustrated by the following examples. The examples are provided for illustrative purposes only, and not to be construed as limiting the scope or content of the invention in any way.

EXAMPLES

Example 1

Expression of Recombinant Folate Receptor Beta

A nucleic acid encoding a fragment of the human folate receptor beta (FRβ) spanning amino acids 22 to 236 (numbering based on sequence in GenBank Accession No. NP_001107007) was cloned from pcDNA3 to baculovirus transfer vector pAcGP67 via Sma I and EcoRI sites. FIG. 1 contains the amino acid sequence (SEQ ID NO:9) of the FRβ protein. Transfer vector pAcGP67 (BD Biosciences Pharmingen) was co-transfected with BaculoGold™ (BD Biosciences Pharmingen) viral DNA into SF9 insect cells according to the manufacturer's instruction.

Recombinant FRβ protein produced from pAcGP67 had four extra residues (ADPG, SEQ ID NO:12) on the N-terminus and five extra histidine residues on the C-terminus. The recombinant FRβ protein was purified from conditioned medium with a nickel-chelating column, and further purified with a SUPERDEX®75 10/300GL gel filtration column in phosphate buffered saline (PBS). The purified protein was >95% purity as estimated by SDS-PAGE. The recombinant FRβ retained its function of binding to folate.

Example 2

Antibody Selection by Phage Display

Purified FRβ was used for panning of a human naïve (not deliberately immunized) Fab phage library. Briefly, 2 μg of FRβ was coated on a Maxisorp plate, which was then incubated with library phage (~$10^{12}$ pfu) for 2 hr. After extensively washing the wells with PBS+0.05% TWEEN®20 (detergent) (PBST), phage were rescued by incubating with exponentially growing TG1 bacteria and helper phage. The panning procedure was repeated three more times with more stringent conditions in the latter two rounds, including decreased amounts of FRβ protein and additional washes with PBST. Three hundred colonies were picked from the last two rounds of panning and rescued with helper phage.

Two clones were selected and further affinity improved by light chain shuffling in which two sub-libraries were made by replacing each light chain sequence with the light chain repertoire from the original library. The sub-libraries then were further panned and screened with FRβ protein as described above.

One clone, m923, identified by this method specifically bound to FRβ protein and contained the heavy chain sequence set forth in SEQ ID NO:7 and the light chain sequence set forth in SEQ ID NO:8.

The clone with the highest affinity, m909, was further characterized as described below. FIGS. 2A and 2B contain the m909 Fab heavy chain sequence (SEQ ID NO:7) and m909 Fab lamba light chain sequence (SEQ ID NO:17), respectively, with the CDR sequences underlined, framework region sequences italicized, and constant region sequence in lowercase, non-italicized text.

The m909 Fab was expressed in *E. coli* HB2151 cells. Soluble Fab was purified from the periplasm using a Ni-chelating column, as the phagemid carries sequences encoding His6 and FLAG tags at the C-terminus of the Fab. A single chain form (scFv) of m909 was made by cloning the VH and VL from the Fab, connected by a linker (GGGGS; SEQ ID NO:13), into pComb3x. Expression and purification of scFv were similar to that of the Fab.

The Fab fragment was converted into an IgG1 molecule by subcloning the heavy chain variable region and the light chain into pDR12 to produce pDR12-m909. See, Bender et al., *Hum Antibodies Hybridomas*, 4:74-9 (1993). FreeStyle™ 293 cells were transfected with pDR12-m909, and IgG1 was secreted into the medium. IgG1 was purified with a protein G column. scFv was purified with a nickel-chelating column. All preparations were dialysed against PBS.

Example 3

Characterization of the m909 Antibody

To characterize the m909 antibody, an ELISA was performed as follows. FRβ, diluted in PBS, was coated on half of the wells of a 96 well plate at 50 ng/well overnight at 4° C. Wells were blocked with 100 μl of 4% milk/PBS (MPBS) for 1 hr at 37° C. For Fab binding kinetics, Fab was titrated from 3000 nM to 0.038 nM (1:5 serial dilutions) then 50 μl of diluted Fab was added to duplicate wells. After 2 hr incubation at 37° C., the wells were washed four times with PBST (PBS+0.05% TWEEN® 20 (detergent)). Bound Fab was detected by incubating with anti-FLAG-horseradish peroxidase (HRP) mAb (1:1000) (Sigma) for 1 hr at 37° C. Wells were washed again with PBST. The HRP substrate 2,2'-azino-bis(3-ethylbenzthiazoline-6-sulphonic acid) (ABTS) was added (50 μl/well), and the absorbance at 405 nm was determined. For ELISA with IgG, a goat anti-human Fc IgG conjugated with HRP was used at 1:1000. FIG. 3 is a graph depicting the binding of m909 $IgG_1$ to FRβ. M909 does not detectably bind to FR alpha (FRα), which shares 70% amino acid identity with FRβ.

FRβ expression of Chinese hamster ovary (CHO)-K1, CHO cells stably transfected with human FRβ (CHO-FRβ), KB nasopharyngeal epidermoid cells, and preB L1.2 cells was determined using folate conjugated to fluorescein isothiocyanate (FITC) (FITC-folate) and mouse mAb 94b. CHO-K1 cells did not detectably express cell surface FRβ while the CHO-FRβ cells had high levels of cell surface FRβ. KB and preB L1.2 cells had low but detectable levels of cell surface FRβ.

Figure 4:
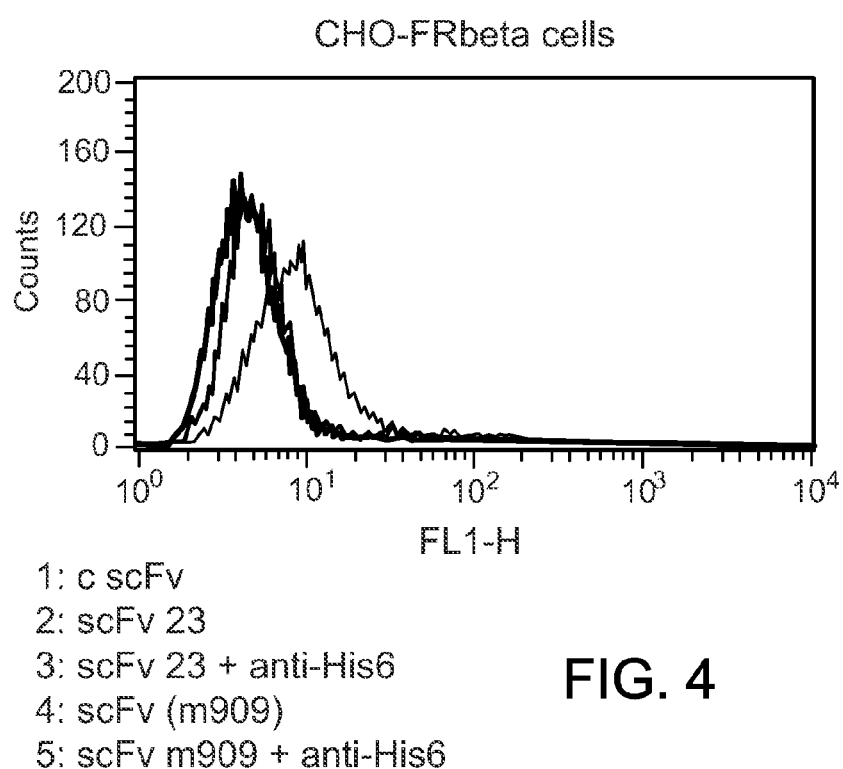
FIG. 4 is a one-dimensional fluorescent flow cytometry (FFC) histogram showing that bivalency allows binding of scFv m909 to FRβ positive cells.
Figure 5:
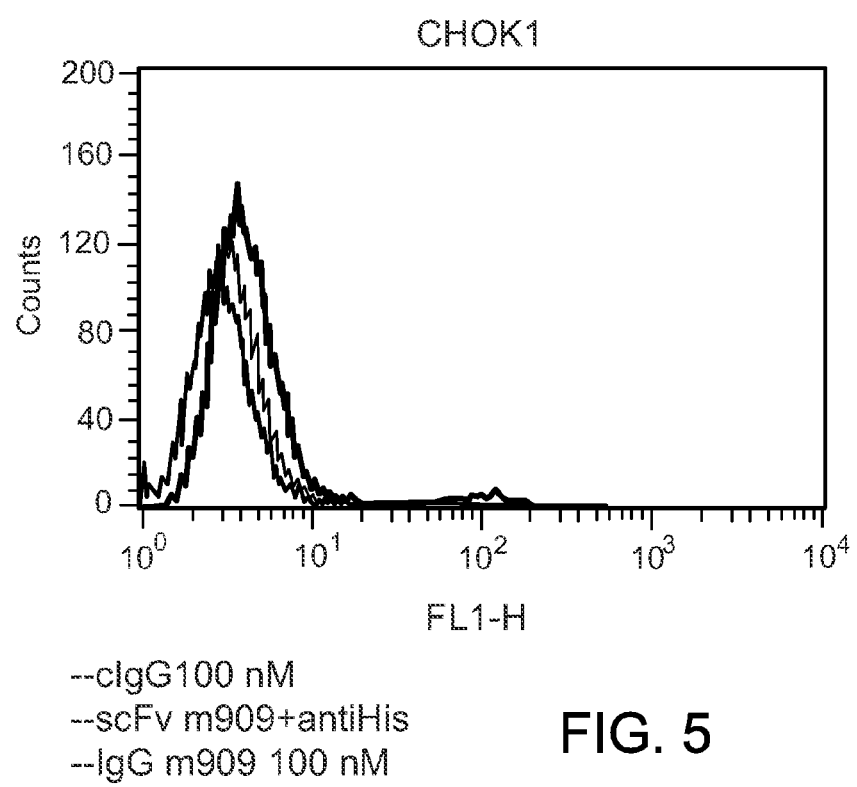
FIG. 5 is a one-dimensional FFC histogram showing that scFv m909 does not bind to FRβ negative cells.

Binding of m909 to cell surface FRβ was determined using FFC on a FACSCalibur (Beckton Dickinson) flow cytometer. Aliquots of cells were incubated with primary antibody (m909, or isotype controls) at the indicated concentrations (see FIGS. 4 and 5) in 250 µl of folate-free RPMI+10% FBS for 1 hr on ice. Unbound antibodies were washed away with folate-free RPMI. Secondary antibody goat anti-human IgG conjugated with FITC (Sigma) was incubated with cells at a concentration of 8 µl/ml for 30 min. m909 Fab and scFv were also pre-incubated with mouse anti-His6 mAb for 30 min at room temperature, before they were added to cells. For detection of Fab or scFv, 1.6 µg/ml of anti-His6 monoclonal antibody (Qiagen) and 8 µl/ml of goat anti-mouse IgG-FITC (Sigma) were incubated with cells. Cells were washed and resuspended in PBS+0.5% BSA for FFC on a FACSCalibur (Beckton Dickinson) flow cytometer. FIG. 4 shows that in FRβ+ cells, the monovalent format of the m909 antibody (scFv) did not bind to cell surface FRβ, whereas the bivalent format, sample 5 (scFv crosslinked by anti-His6 mAb) shows binding. Fab also does not bind to FRβ. FIG. 5 indicates that in FRβ– cells, neither the monovalent format (scFv) nor bivalent format (IgG) of m909 shows detectable binding.

Figure 6A:
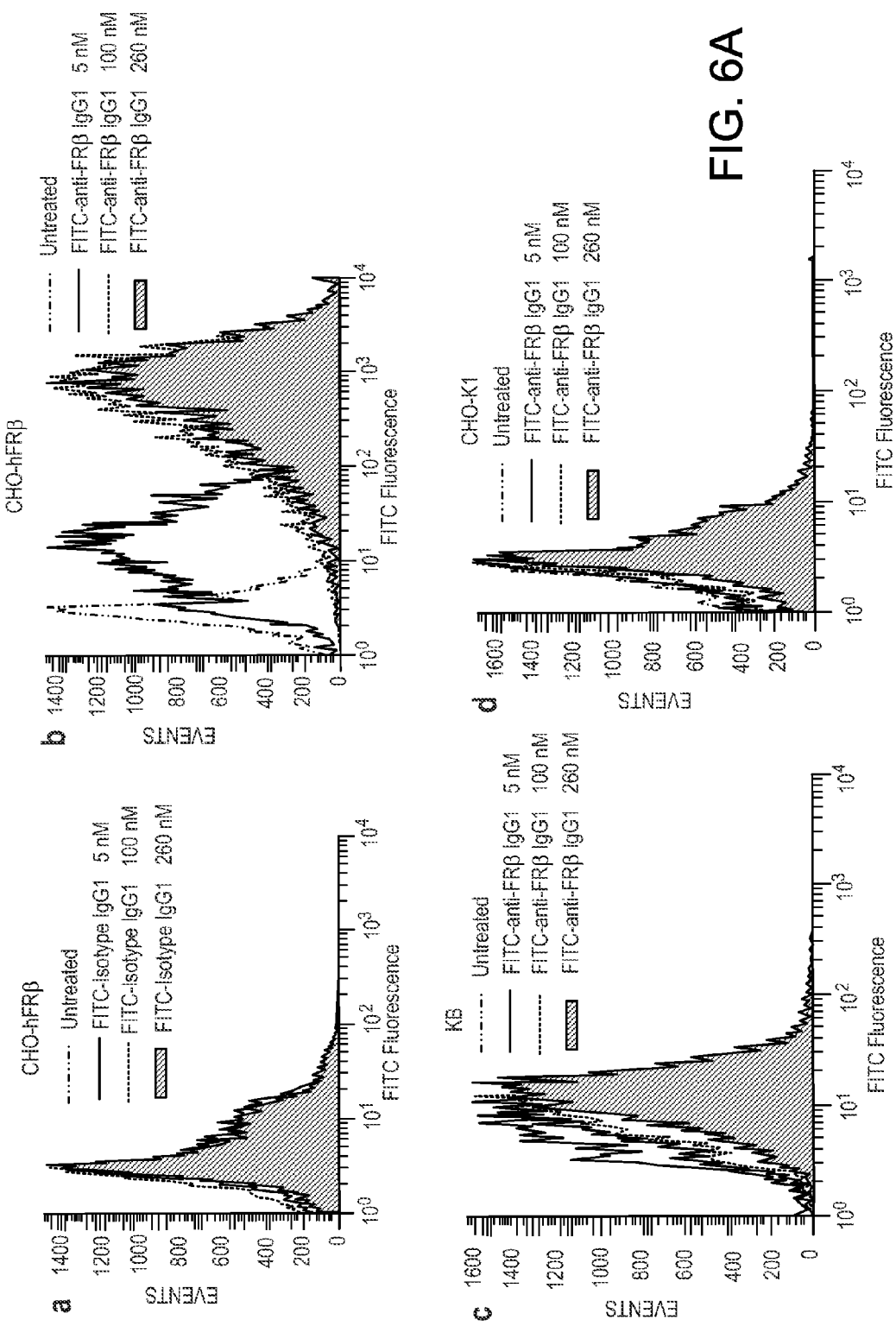
FIGS. 6A and 6B depict isoform-specific binding of FITC-human anti-human FRβ mAb to FRβ-positive/negative cell lines.
Figure 6B:
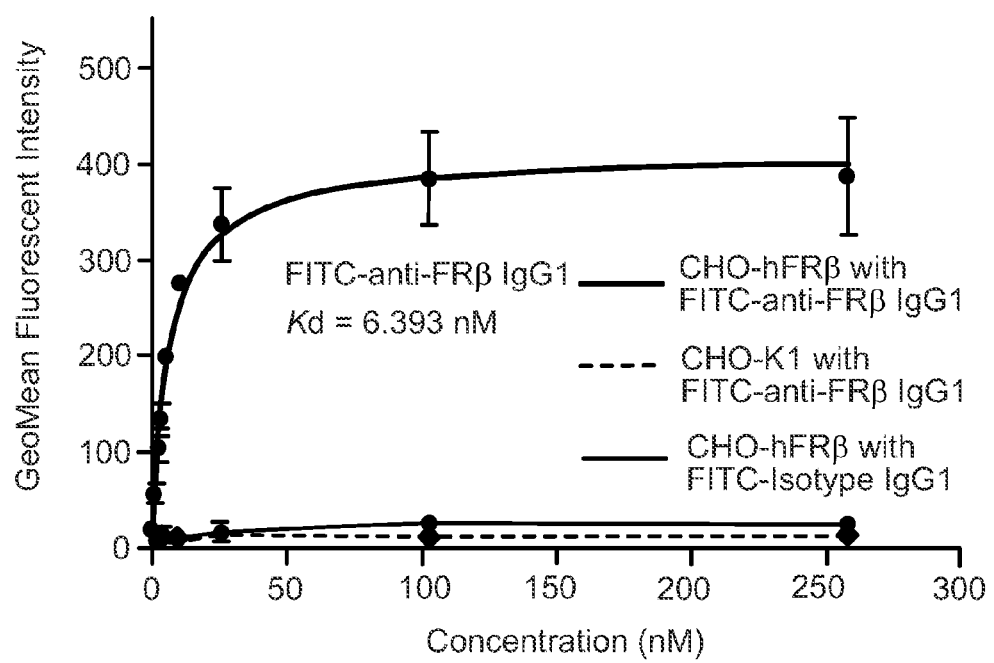

FIGS. 6A and 6B show the concentration-dependent binding of m909 IgG to FRβ+ cells. In FIG. 6A, CHO-FRβ cells (a) were incubated with serial concentrations of control FITC-Isotype IgG1, and CHO-FRβ cells (b), KB cells (c), and CHO-K1 cells (d) were incubated with serial concentrations of control FITC-anti-FRβ IgG1. m909 bound to FRβ-positive cell lines. FIG. 6B is a graph depicting affinity of FITC-anti-FRβ IgG1 for CHO-FRβ cells. Saturation binding fit gave a dissociation constant (Kd) of 6.393 nM, which is the concentration of free FITC-anti-FRβ IgG1 that would half-saturate FRβ on the cell surface.

Example 4

Cell Lysis by Antibody-Dependent Cell-Mediated Cytotoxicity

Peripheral blood mononuclear cells (PBMC) were isolated from healthy human donors with Ficoll-Paque Plus (GE Healthcare). Collections of blood from donors were approved by NCI-Frederick Research Donor Program. The viability of isolated cells was >95%. PBMC were seeded in a 96 well plate in RPMI+10% FBS at 500,000 cells/well. Cells were incubated at 37° C. and allowed to attach to the plate for 3 hr. Unattached cells were rinsed off by two washes of warm PBS, cells attached in the wells were used as the effector cells. Target cells (CHO-K1, CHO-FRβ, or preB L1.2 cells) were trypsinized and resuspended into single cell suspensions. The target cells were incubated with various concentrations of m909 IgG or control IgG at room temperature for 30 min then added to effector cells at 10,000 cells/well. The ratio of effector and target cells was 50:1. The plate was centrifuged at 300 g×5 min and incubated at 37° C. for 24 hr. Supernatant (100 µl) was transferred to an all-white plate and 100 µl of CYTO-TOX-ONE™ membrane integrity assay reagent (Promega) was added to each well. Lactate dehydrogenase (LDH) released from lysed cells converted the CytoTox substrate to fluorescent resorufin, which was measured in a fluorometer at the emission wavelength of 590 nm (excitation wavelength is 530-560 nm). The percentage of specific lysis was calculated as the fluorescence of (experimental treatment-effector cell control)/(high control-target cell control)×100%. Fluorescence of target cells alone treated with 1% TRITON® X-100 (detergent) was used as high control. Each treatment was carried out in 6 replicate wells. Each assay plate included control wells.

Figure 7:
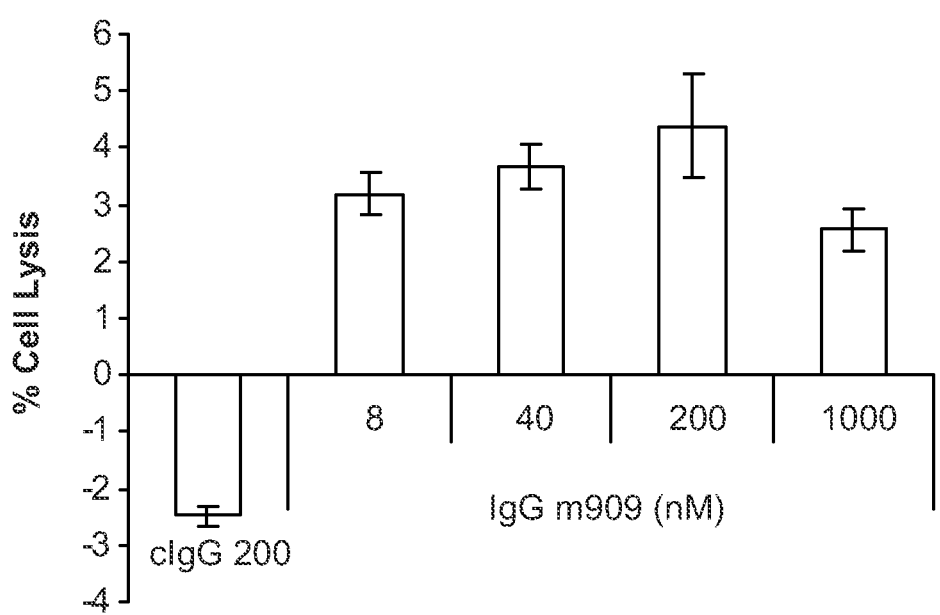
FIG. 7 is a bar graph showing the percent lysis of preB L1.2 FRβ-positive cells at various concentrations of $IgG_1$ m909 or control $IgG_1$.
Figure 8:
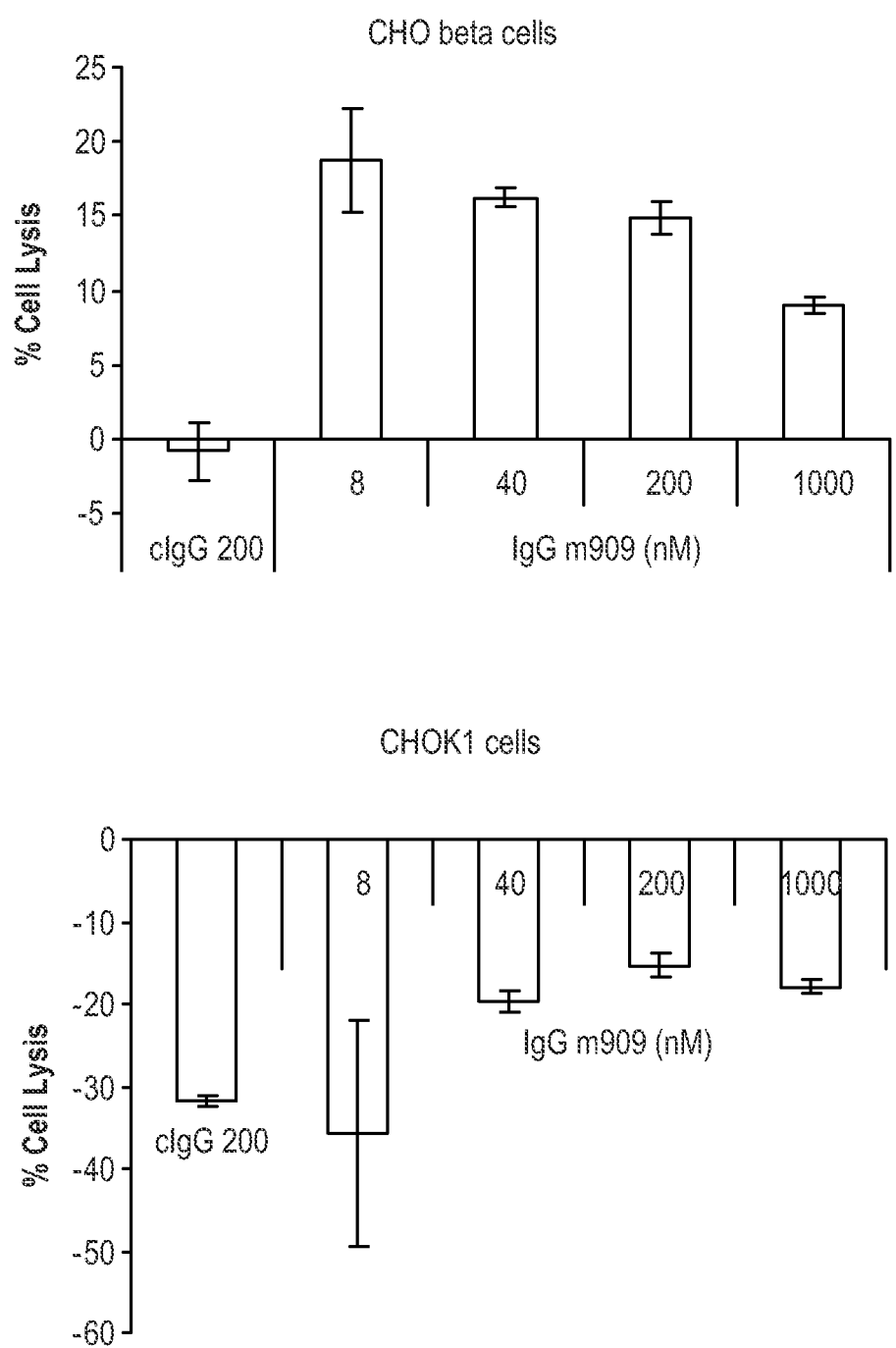
FIG. 8 contains a bar graph of the percent lysis of CHO-FRβ cells (left panel) and a bar graph of the percent lysis of CHO-K1 cells (right panel).

FIGS. 7 and 8 indicate that m909 induced ADCC was correlated with the level of surface FRβ expression. In preB L1.2 cells, cell surface FRβ expression was positive but low, and ADCC was detectable at approximately 5% (see FIG. 7). In CHO-FRβ cells, expression of surface FRβ was much higher, and m909 induced approximately 20% of cell lysis (see FIG. 8).

Example 5

Figure 9A:
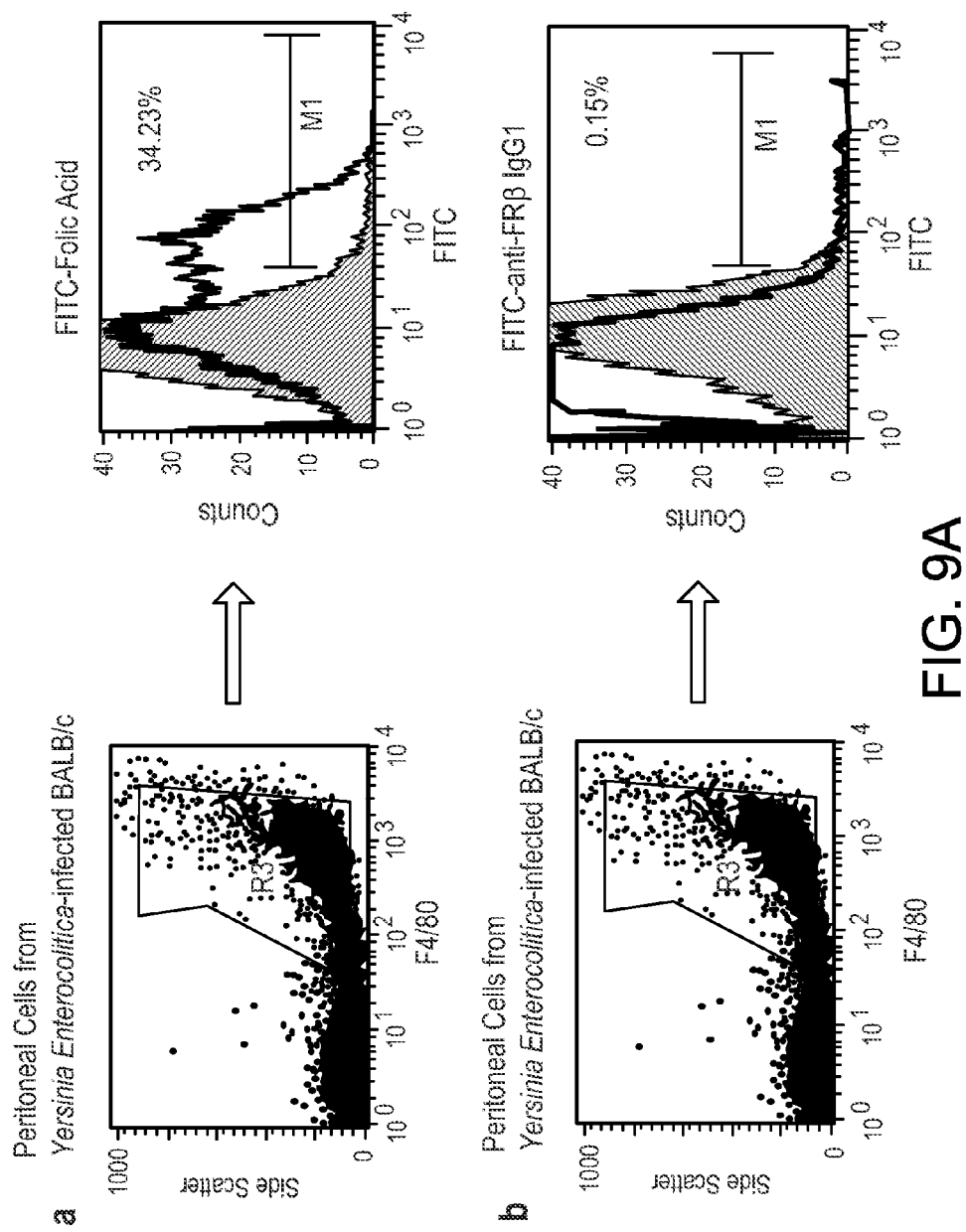
FIG. 9A contains representative 2-dimensional and 1-dimensional FFC analyses of FITC-anti-FRβ m909 IgG1 binding to bacteria-recruited peritoneal FRβ+ macrophages. In a), FRβ+ macrophages were stained with folate conjugated to FITC. In b), FRβ+ macrophages were stained with FITC conjugated to human anti-human FRβ m909 IgG1. The percentage of FRβ+ cells within each gate shown in the left hand two panels (2-dimensional FFC histograms) are shown in the right hand two panels (1-dimensional FFC histograms).

Species-Specific Binding of Human Anti-Human FRβ Monoclonal Antibody to FRβ Positive Cells Live *Yersinia enterocolitica* bacterial cells were injected intraperitoneally (IP) into BALB/c mice to recruit peritoneal FRβ+ macrophages. Three days after the IP injection, peritoneal cells were removed and analyzed by flow cytometry using F4/80 macrophage specific antibody. The cells were stained with either (a) 100 nM Folate-FITC in the absence (solid black histogram) or presence of an excess (10 µM) of free folic acid to competitively occupy FR (filled gray histogram) or (b) 5 nM FITC-anti-human FRβ m909 IgG1 (solid black histogram) or 5 nM control FITC-Isotype IgG1 (filled gray histogram). The percentage of FRβ+ cells within each gate is shown in FIG. 9A. While there were approximately 34.23% of FRβ+ cells present (see top panel of FIG. 9A), staining with FITC conjugated anti-human FRβ m909 IgG1 detected only 0.15% of FRβ+ cells present.

Figure 9B:
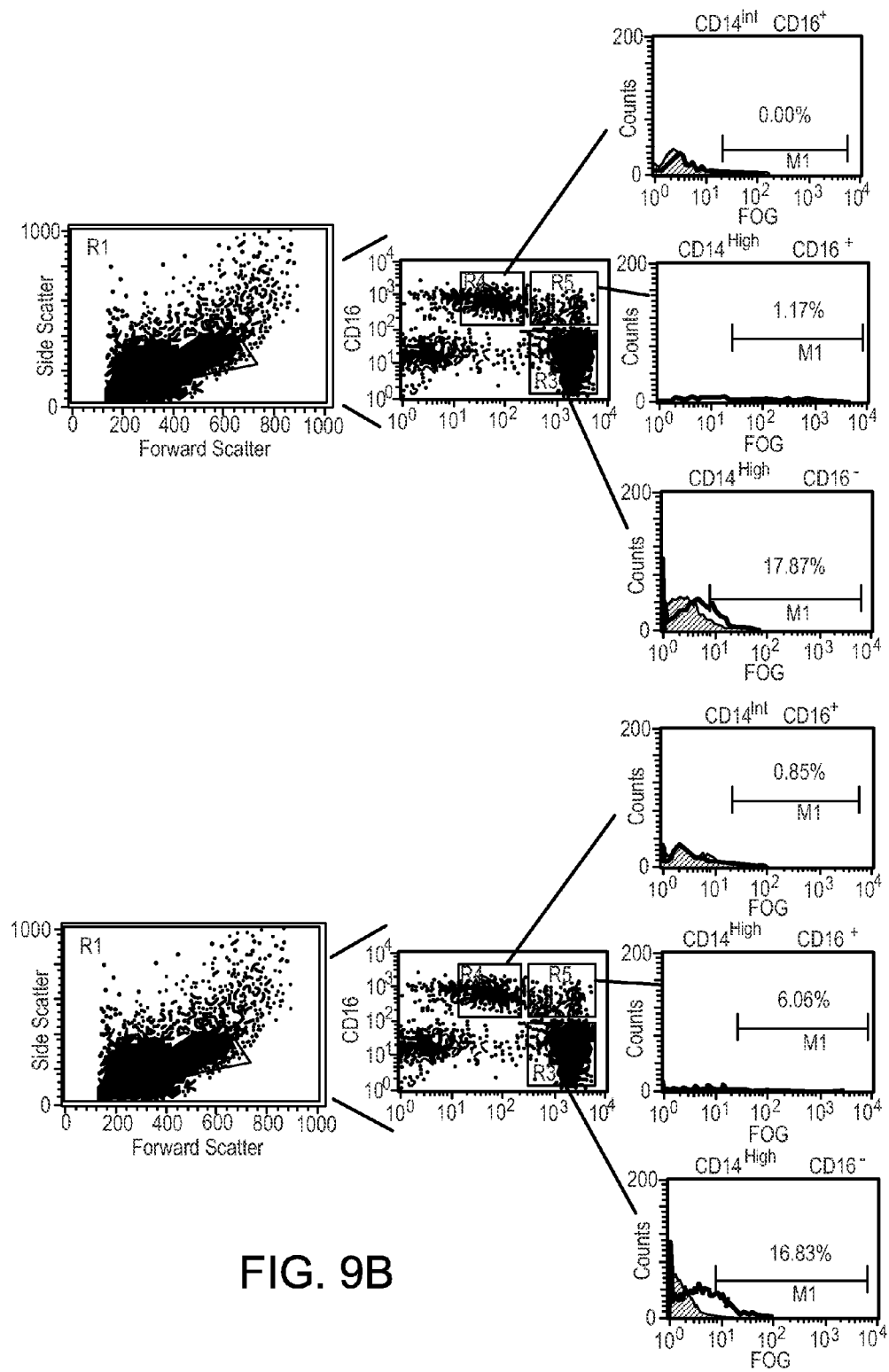
FIG. 9B contains representative 2-dimensional and one-dimensional FFC analyses of FITC-anti-FRβ m909 IgG1 binding to the FRβ+ CD14$^{High}$ CD16$^-$ subset of human peripheral blood monocytes. The populations of cells gated in the left hand 2-dimensional histograms were subjected to analysis using fluorochrome-conjugated anti-CD16 and anti-CD14 antibodies (middle two 2-dimensional FFC histograms) and the percentage of FRβ+ cells in the gated populations in the latter histograms were determined (right hand 1-dimensional FFC histograms).

Human peripheral blood mononuclear cells (PBMCs) were stained with folate conjugated to Oregon Green (FOG) and both phycoerythrin (PE)-anti-CD14 and Tricolor-anti-CD16 antibodies. In the experiments shown in FIG. 9B, the cells were stained with (a) 100 nM FOG in the absence (solid black histogram) or presence of an excess (10 µM) of free folic acid to competitively occupy FR (filled gray histogram) or (b) 5 nM FITC-anti-FRβ m909 IgG1 (solid black histogram) or 5 nM control FITC-Isotype IgG1 (filled gray histogram). The percentage of FRβ+ cells within each gate is shown in FIG. 9B. FITC-anti-FRβ m909 IgG1 bound selectively to $CD14^{high}$, CD16− monocytes.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated human monoclonal antibody, or an antigen-binding fragment thereof, that specifically binds human folate receptor β (FRβ), the antibody or fragment comprising:
   a heavy chain variable region ($V_H$) CDR 1 comprising the amino acid sequence set forth in SEQ ID NO:1;
   a $V_H$ CDR2 comprising the amino acid sequence set forth in SEQ ID NO:2;
   a $V_H$ CDR3 comprising the amino acid sequence set forth in SEQ ID NO:3;
   a light chain variable region ($V_L$) CDR1 comprising the amino acid sequence set forth in SEQ ID NO:14;
   a $V_L$ CDR2 comprising the amino acid sequence set forth in SEQ ID NO:15; and
   a $V_L$ CDR3 comprising the amino acid sequence set forth in SEQ ID NO:16.

2. The antibody or fragment of claim 1, wherein the antibody or fragment has one or more properties selected from the group consisting of:
   (a) the antibody or fragment does not detectably bind to human folate receptor alpha (FRα);
   (b) the antibody or fragment binds to human macrophages but not to mouse macrophages;
   (c) the antibody or fragment has a binding affinity of 20 nM;
   (d) the antibody or fragment has a dissociation constant (Kd) of 6.39 nM; and
   (e) the antibody mediates antibody-dependent cellular cytotoxicity (ADCC) of FRβ-expressing target cells.

3. The antibody or fragment of claim 1, wherein said antibody or fragment binds to cell surface FRβ.

4. The antibody or fragment of claim 1, wherein said antibody is an IgG1 antibody.

5. The antibody or fragment of claim 1, wherein said antibody or fragment is de-fucosylated.

6. The antibody or fragment of claim 1, wherein the fragment is a Fab antibody fragment, a F(ab')$_2$ fragment, or a single chain antibody fragment (scFv).

7. The antibody or fragment of claim 1, wherein said antibody or fragment is conjugated with a pharmaceutical agent 8. The antibody or fragment of claim 7, wherein said pharmaceutical agent is a chemotherapeutic.

9. The antibody or fragment of claim 1, wherein said antibody or fragment is conjugated to a liposome.

10. The antibody or fragment of claim 9, wherein said liposome comprises a pharmaceutical agent.

11. The antibody or fragment of claim 1, wherein said antibody or fragment is linked to a toxin.

12. The antibody or fragment of claim 11 wherein said antibody or fragment thereof is covalently linked to said toxin.

13. The antibody or fragment of claim 1, wherein said antibody or fragment is linked to a detectable moiety.

14. The antibody or fragment of claim 13, wherein said detectable moiety is selected from the group consisting of a fluorescent moiety, a luminescent moiety, a radioactive moiety, a CT contrast agent, an MRI contrast agent, and biotin.

15. The antibody or fragment of claim 1, wherein the antibody or fragment comprises SEQ ID NO:10.

16. A composition comprising the antibody or fragment of claim 1 and a pharmaceutically acceptable carrier.

17. The antibody or fragment of claim 1, wherein the antibody or fragment comprises SEQ ID NO:18.

* * * * *

UNITED STATES PATENT AND TRADEMARK OFFICE
CERTIFICATE OF CORRECTION

PATENT NO.       : 8,871,206 B2
APPLICATION NO.  : 13/790881
DATED            : October 28, 2014
INVENTOR(S)      : Philip S. Low et al.

Page 1 of 1

It is certified that error appears in the above-identified patent and that said Letters Patent is hereby corrected as shown below:

On the Title Page Item (63) in Related U.S. Application Data:

Delete "Continuation" and insert -- Continuation-in-part --, therefor.

Signed and Sealed this
Twenty-fourth Day of February, 2015

Michelle K. Lee
*Deputy Director of the United States Patent and Trademark Office*